(12) United States Patent
Poliniak et al.

(10) Patent No.: US 6,511,712 B1
(45) Date of Patent: Jan. 28, 2003

(54) METHODS USING DRY POWDER DEPOSITION APPARATUSES

(75) Inventors: Eugene Samuel Poliniak, Willingboro, NJ (US); Hoi Cheong Steve Sun, Monmouth Junction, NJ (US); Nitin Vithalbhai Desai, Princeton Junction, NJ (US); Nalin Kumar, Cherryhill, NJ (US); William Ronald Roach, Rocky Hill, NJ (US); Lawrence Harrison Hammer, Plainsboro, NJ (US); Peter David Southgate, Kingston, NJ (US); Bawa Singh, Voorhees, NJ (US); Howard Christopher Rivenburg, Princeton, NJ (US); Peter Zanzucchi, Lawrenceville, NJ (US); David Keller, Newtown, PA (US); Dominic Stephen Rosati, Hamiton, NJ (US)

(73) Assignee: Delsys Pharmaceutical, Monmouth Junction, NJ (US)

( * ) Notice: Subject to any disclaimer, the term of this patent is extended or adjusted under 35 U.S.C. 154(b) by 0 days.

(21) Appl. No.: 09/531,639

(22) Filed: Mar. 21, 2000

Related U.S. Application Data

(62) Division of application No. 09/095,246, filed on Jun. 10, 1998, now Pat. No. 6,063,194.

(51) Int. Cl.⁷ .................................................. B05D 1/04
(52) U.S. Cl. ........................ 427/466; 427/469; 427/475; 427/485
(58) Field of Search ................................. 427/466, 469, 427/475, 477, 478, 485; 118/668, 665, 629, 627, 628; 279/128; 361/234

(56) References Cited

U.S. PATENT DOCUMENTS

| 1,121,452 | A | | 12/1914 | Bagnall |
|---|---|---|---|---|
| 2,936,851 | A | * | 5/1960 | Cook |
| 4,072,129 | A | * | 2/1978 | Bright et al. |
| 4,090,666 | A | * | 5/1978 | Peck |
| 4,160,257 | A | | 7/1979 | Carrish |
| 4,197,289 | A | | 4/1980 | Sturzenegger et al. |
| 4,332,789 | A | | 6/1982 | Mlodozeniec |
| 4,349,531 | A | | 9/1982 | Mlodozeniec et al. |
| 4,502,094 | A | | 2/1985 | Lewin et al. |
| 4,554,611 | A | | 11/1985 | Lewin |
| 4,561,688 | A | | 12/1985 | Tsutsui |
| 4,652,318 | A | | 3/1987 | Masuda et al. |
| 4,685,620 | A | | 8/1987 | Law et al. |
| 4,779,564 | A | | 10/1988 | Kiefer et al. |
| 4,816,285 | A | * | 3/1989 | Ribnitz |
| 4,860,417 | A | | 8/1989 | Tajima et al. |
| 4,917,978 | A | | 4/1990 | Ritt et al. |
| 4,921,727 | A | | 5/1990 | Datta et al. |
| 4,921,767 | A | | 5/1990 | Datta et al. |

(List continued on next page.)

FOREIGN PATENT DOCUMENTS

JP    57-196211    2/1982

OTHER PUBLICATIONS

Powder Coating The Complete Finisher's Handbook, Ed by N.P. Liberto, pp. 95–96, 1994.*

(List continued on next page.)

Primary Examiner—Fred J. Parker
(74) Attorney, Agent, or Firm—Dechert

(57) ABSTRACT

Provided is a method using a dry deposition apparatus for depositing grains on a substrate comprising:
- an electrostatic chuck having one or more collection zones, wherein the substrate is layered on the chuck for processing;
- a charged grain delivery apparatus for directing charged grains for electrostatic deposition on the substrate at the locations of the collection zones; and
- an optical detection device for quantifying the amount of grains deposited.

18 Claims, 16 Drawing Sheets

U.S. PATENT DOCUMENTS

| | | | |
|---|---|---|---|
| 4,948,497 | A | 8/1990 | Ohkawa |
| 4,971,257 | A | 11/1990 | Birge |
| 5,028,501 | A | 7/1991 | Ritt et al. |
| 5,080,380 | A | 1/1992 | Nakagawa et al. |
| 5,102,690 | A | 4/1992 | Iyer et al. |
| 5,126,165 | A * | 6/1992 | Akihama et al. ........... 427/53.1 |
| 5,310,582 | A | 5/1994 | Vyakarnam et al. |
| 5,463,525 | A | 10/1995 | Barnes et al. |
| 5,522,131 | A | 6/1996 | Steger |
| 5,534,309 | A | 7/1996 | Liu |
| 5,669,973 | A | 9/1997 | Pletcher |
| 5,714,007 | A | 2/1998 | Pletcher et al. |
| 5,753,303 | A | 5/1998 | Sun et al. |
| 5,788,814 | A | 8/1998 | Sun et al. |
| 5,846,595 | A * | 12/1998 | Sun et al. |
| 5,857,456 | A | 1/1999 | Sun et al. |
| 5,858,099 | A | 1/1999 | Sun et al. |
| 5,871,010 | A | 2/1999 | Datta et al. |
| 5,988,432 | A | 11/1999 | Sun |
| 6,007,630 | A | 12/1999 | Pletcher et al. |
| 6,074,688 | A | 6/2000 | Pletcher et al. |
| 6,096,368 | A | 8/2000 | Sun |
| 6,149,774 | A | 11/2000 | Sun |
| 6,294,024 | B1 | 9/2001 | Sun et al. |

OTHER PUBLICATIONS

Daviet et al., "Electrostatic Clamping Applied to Semiconductor Plasma Processing–I. Theoretical Modeling," *J. Electrochem. Soc.*, 140(11):3245–3256, Nov. 1993.

Daviet et al., "Electrostatic Clamping Applied to Semiconductor Plasma Processing–II. Experimental Results," *J. Electrochem. Soc.*, 140(11):3256–3261, Nov. 1993.

Field, "Electrostatic wafer clamping for next–generation manufacturing," *Solid State Technology*, pp. 91–98, Sep. 1994.

Hartsough, "Electrostatic Wafer Holding," *Solid State Technology*, pp. 87–90, Jan., 1993.

Nakasuji et al., "Low voltage and high speed operating electrostatic wafer chuck using sputtered tantalum oxide membrane," *J. Vac. Sci. Technol. A*, 12(5):2834–2839, Sep./Oct., 1994.

Seanor, "Triboelectrification Of Polymers," in K.C. Frisch and A. Patsis, Electrical Properties of Polymers, *Technomic Publications*, Westport, CT, pp. 37–58.

Singer, "Electrostatic Chucks in Wafer Processing," *Semiconductor International*, pp. 57–64, Apr., 1995.

Watanabe et al., "Electrostatic charge distribution in the dielectric layer of alumina electrostatic chuck," *Journal of Materials Science*, 29:3510–3516, 1994.

Watanabe et al., "Electrostatic Force and Absorption Current of Alumina Electrostatic Chuck," *J. Appl. Phys.*, 31(7): 2145–2150, Jul., 1992.

* cited by examiner

ULTRADOSE SYSTEM
FRONT VIEW

METHODS USING DRY POWDER DEPOSITION APPARATUSES

This application is a division and claims priority of U.S. application Ser. No. 09/095,246, filed Jun. 10, 1998 now U.S. Pat. No. 6,063,194, issued May 16, 2000.

The present invention relates to a dry powder deposition apparatus, and methods and apparatuses employed in the dry powder deposition apparatus.

Certain of the applicants have previously described apparatuses and techniques for using electromagnetic forces to make controlled depositions of materials. Such depositions make it possible to deposit controlled amounts of, for example, a pharmaceutical onto spatially resolved areas of a substrate. Described herein are further improvements to the methods and techniques for controlled deposition, and a machine that integrates a number of technologies for making controlled depositions.

SUMMARY OF THE INVENTION

The invention provides a dry deposition apparatus for depositing grains on a substrate comprising:
- an electrostatic chuck having one or more collection zones, wherein the substrate is layered on the chuck for processing;
- a charged grain delivery apparatus for directing charged grains for electrostatic deposition on the substrate at the locations of the collection zones; and
- an optical detection device for quantifying the amount of grains deposited.

Preferably, the optical detection device is: a diffuse reflectance system; and/or an integrated diffuse reflectance and profilometry system. To better assure deposition and optical detection are aligned, the apparatus can further comprise:
- alignment brackets into which the substrates are fitted; and
- alignment devices at the charged grain delivery apparatus and at the optical detection device which interact with the alignment bracket to assure that the collection zone-corresponding regions of the substrate are reproducibly placed.

Also provided is a dry deposition apparatus for depositing grains on a substrate comprising:
- an electrostatic chuck having one or more collection zones, wherein the substrate is layered on the chuck for processing;
- a charged grain delivery apparatus for directing charged grains for electrostatic deposition on the substrate at locations corresponding to the locations of the collection zones;
- a electronic processor for controlling depositions; and
- sensor inputs to the electronic processor including one or more deposition sensors placed on or adjacent to the electrostatic chuck for measuring the amount of grains deposited at the deposition sensors;

wherein the electronic processor responds to data from the sensors to adjust current deposition parameters including flux of grains through the grain delivery apparatus and voltages applied at one or more collection zones to attract grains. In one embodiment, the sensor inputs further include inputs measuring for the flux of grains through the grain delivery apparatus. Another embodiment further comprises:
- a post-deposition detection device for detecting the amount of grains deposited at locations corresponding to the locations of the collection zones;

wherein the deposition data is sent to the electronic processor, which uses the data to adjust current deposition parameters.

Further provided is a dry deposition apparatus for depositing grains on a substrate comprising:
- an electrostatic chuck, wherein the substrate is layered on the chuck for processing;
- a movable receiver on which the electrostatic chuck is mounted, which comprises a high voltage board for creating high voltages for operating the electrostatic chuck, wherein the high voltages are localized near the electrostatic chuck where such voltages are needed. The dry deposition apparatus can further comprise:
- an electronic processor for controlling depositions, wherein the movable receiver further comprises an addressing board which receives operating signals from the electronic processor and parses out locations on the electrostatic chuck to receive a voltage or voltage adjustment and the amplitude of the voltage or voltage adjustment, and sends this information to appropriate channels of the high voltage board.

Also provided is a dry deposition apparatus for depositing grains on a substrate comprising:
- an electrostatic chuck, wherein the substrate is layered on the chuck for processing; and
- a grain feed apparatus comprising:
  - a tube for delivering grains towards the electrostatic chuck;
  - a mechanical device for moving the grains having an outlet for inserting the grains towards the tube; and
  - one or more of:
    - a gas driven Venturi having a Venturi well for pulling grains from the mechanical device and propelling, with the gas, the grains through the tube, or
    - a gas source for directing gas towards the outlet of the mechanical device to separate grains exiting the mechanical device and provide gas flow propelling grains through the tube.

Further provided is a dry deposition apparatus for depositing grains on a substrate comprising:
- an electrostatic chuck, wherein the substrate is layered on the chuck for processing; and
- a grain feed apparatus comprising:
  - a tube for delivering grains towards the electrostatic chuck; and
  - a baffle at the outlet of the tube for enhancing uniformity of a cloud of grains directed by the grain feed apparatus towards the electrostatic chuck.

Another dry deposition apparatus for depositing grains on a substrate comprises:
- an electrostatic chuck, wherein the substrate is layered on the chuck for processing; and
- a grain feed apparatus comprising a tube for delivering grains towards the electrostatic chuck, wherein the tube applies charge to the grains by tribocharging or induction charging.

The dry deposition apparatus can further comprise:
- a electronic processor for controlling depositions; and
- a monitor for measuring the amount of charge discharged from the tube, wherein the electronic processor utilizes data from the monitor as an indicator of the amount of grains passing through the tube.

Also provided is a dry deposition apparatus for depositing grains on a substrate comprising:

an electrostatic chuck, wherein the substrate is layered on the chuck for processing;

a grain feed apparatus for delivering grains towards the electrostatic chuck; and a powder trap for recovering grains directed to the electrostatic chuck which are not adhered thereto, comprising a series of conductive baffles, with some baffles having a positive potential and others having a negative potential.

The dry deposition apparatus for depositing grains on a substrate can comprise: a diffuse reflection optical detection device for measuring the amount of grains deposited on the substrate and/or an optical profilometer for measuring the amount of grains deposited on the substrate.

Also provided is dry deposition apparatus for depositing grains on a substrate comprising:

an electrostatic chuck having one or more collection zones, wherein the substrate is layered on the chuck for processing;

a charged grain delivery apparatus for directing charged grains for electrostatic deposition on the substrate at the locations of the collection zones; and a sealing apparatus for sealing a covering substrate onto grain-coated locations of the first substrate.

BRIEF DESCRIPTION OF THE DRAWINGS

FIG. 8A shows an electrostatic chuck adhered to the underside of a receiver, while

FIG. 15A shows a schematic illustration of diffuse relection for characterizing dry powders; while

DETAILED DESCRIPTION OF THE INVENTION

Several copending applications or issued patents provide information on dry deposition techniques. For example, methods for use of bead transporter chucks and acoustic grain dispensers are set forth in Pletcher et al., "Apparatus for electrostatically depositing a medicament powder upon predefined regions of a substrate," U.S. Pat. No. 5,714,007, issued Feb. 3, 1998; Pletcher et al., "Method and apparatus for electrostatically depositing a medicament powder upon predefined regions of a substrate," U.S. Pat. No. 6,007,630, issued Dec. 28, 1999; Pletcher et al., "Method and apparatus for electrostatically depositing a medicament powder upon predefined regions of a substrate," U.S. Pat. No. 6,074,688, issued Jun. 30, 2000; Pletcher et al., "Apparatus for electrostatically depositing and retaining materials upon a substrate" U.S. Pat. No. 5,669,973, issued Sep. 23, 1997; Datta et al., "Inhaler apparatus with modified surfaces for enhanced release of dry powders," U.S. Pat. No. 5,871,010, issued Feb. 16, 1999; Sun et al., "Acoustic dispenser" U.S. Pat. No. 5,753,302) issued May 19, 1998; Sun et al., "Electrostatic Chucks," U.S. Pat. No. 5,846,595, issued Dec. 8, 1998; Sun et al, "Electrostatic Chucks," U.S. Pat. No. 5,858,099, issued Jan. 12, 1999; Sun, "Chucks and Methods for Positioning Multiple Objects on a Substrate," U.S. Pat. No. 5,788,814, issued Aug. 4, 1998; Loewy et al., "Deposited Reagents for Chemical Processes," U.S. application Ser. No. 08/956,737, filed Oct. 23, 1997, now U.S. Pat. No. 6,045,753; Loewy et al., "Solid Support With Attached Molecules," U.S. application Ser. No. 08/956,348, filed Oct. 23, 1997, now U.S. Pat. No. 6,004,752; Sun, "Bead Transporter Chucks Using Repulsive Field Guidance," U.S. Pat. No. 6,096,368, issued Aug. 1, 2000; Sun, "Bead manipulating Chucks with Bead Size Selector," U.S. Pat. No. 5,988,432, issued Nov. 23, 1999; Sun, "Focused Acoustic Bead Charger/Dispenser for Bead Manipulating Chucks," U.S. Pat. No. 6,168,666, issued Jan. 2, 2001. Additional instructional information is found in Sun et al., "AC waveforms biasing for bead manipulating chucks," U.S. application Pat. No. 6,149,774, issued Nov. 21, 2000;, Sun et al., "Apparatus for Clamping a Planar Substrate," U.S. application Ser. No.

09/095,321, filed Jun. 10, 1998; and "Pharmaceutical Product and Method of Making," U.S. Pat. No. 6,303,143.

Basic Elements of Robotic Platform

Figure 1:
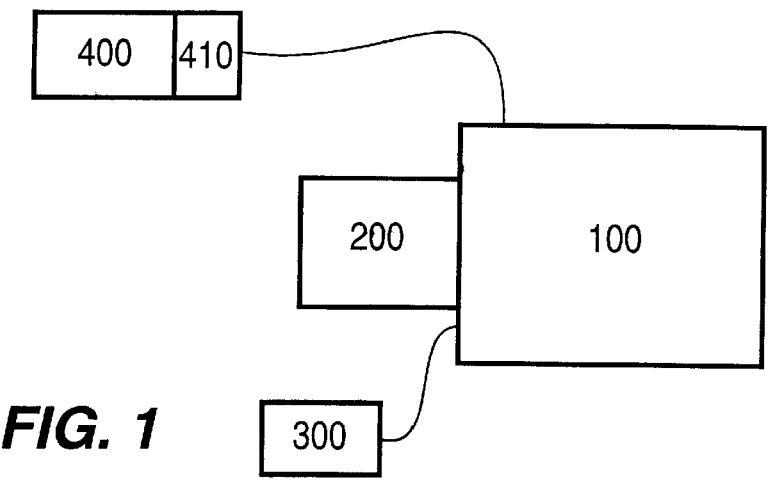
FIG. 1 shows a schematic of a robotic platform, a grain feed apparatus, environmental controller, and a central electronic processor, which components can be used in the present invention.

Elements of an exemplary dry powder deposition apparatus are illustrated schematically in FIG. 1. FIG. 1 shows a robotic platform 100 at which substrates, such as planar substrates, which are optionally mounted in a frame, are processed to dry deposit grains (e.g., powder), preferably, on defined regions of the substrates. The robotic platform 100, which is preferably in an environmental enclosure, can include (1) a substrate input/output station at which substrates and lamination covers are held ready for use by robotic transport elements, or processed substrates are held for later use or further processing, (2) an alignment station at which framed substrates and lamination covers are aligned with the robot probe that manipulates them, (3) a station for such deposition, (4) a dose measurement station, and (5) a lamination station. Charged grains are delivered to the robotic platform 100 from grain feed apparatus 200, which is also preferably in an environmental enclosure. Environmental controller 300 is used to control the temperature, pressure and humidity within the robotic platform 100. Electronic components for operating various electronic equipment in the dry deposition apparatus can be housed in electronic cabinet 400, including a central electronic processor 410.

Figure 2:
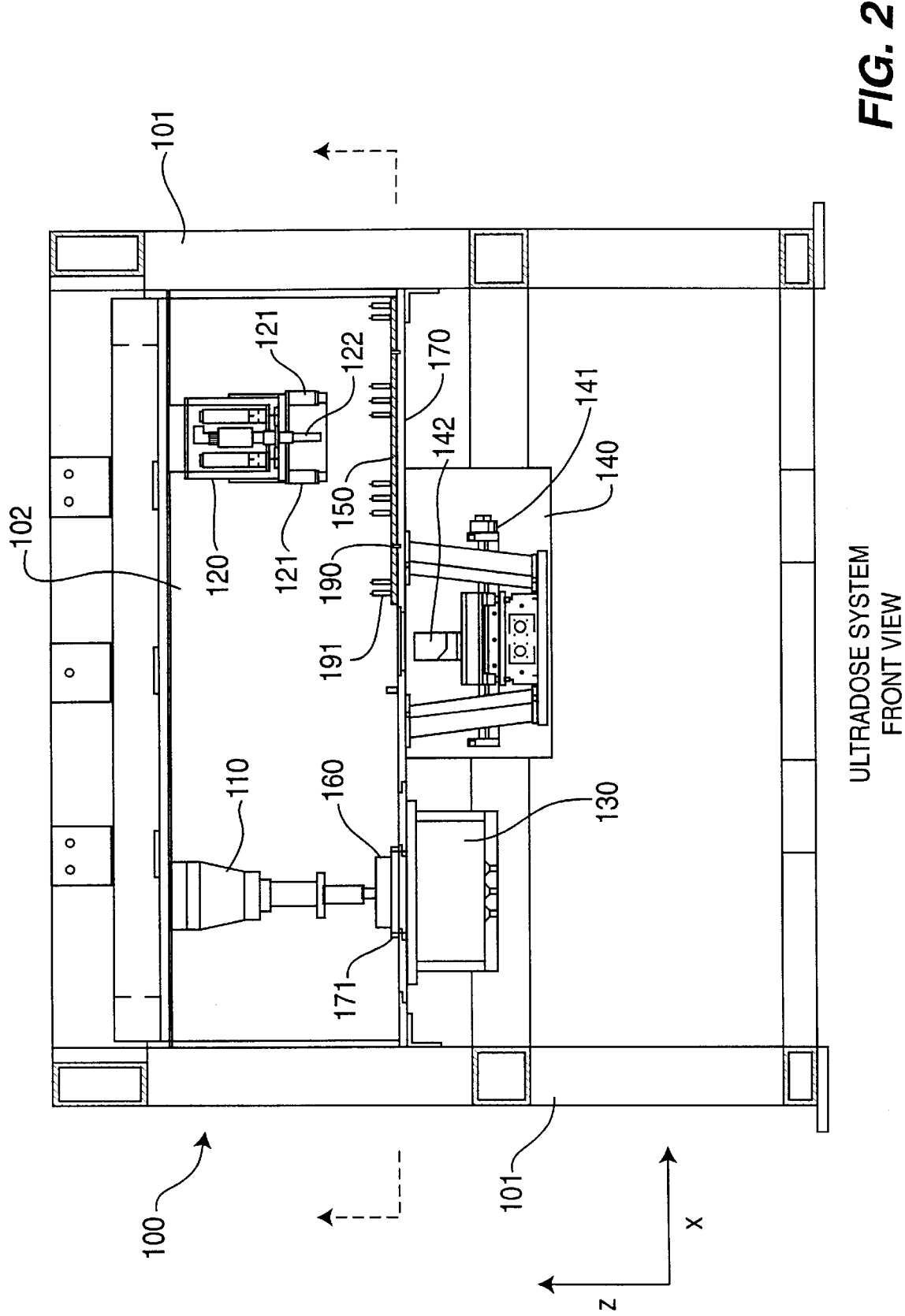
FIG. 2 shows a side view of a robotic platform which can be used to step a substrate through the deposition process.

Robotic platform 100 can be based, for example, on a Yaskawa RobotWorld Linear Motor Robot (Yaskawa Electric Company, Japan). As illustrated in FIG. 2, robot platform 100 has a first probe 110 and a second probe 120. The probes (110 and 120) are linked to first rails (e.g., x-axis rails) that provide guides for motion in one direction. Additional rails (not shown) moveably mounted on the first rails provide support for motion in a direction orthogonal to the first set of rails, to provide x-y motion. X-y motion is effected with x-y linear stepper motors. First probe 110 and second probe 120 have telescoping components under servo control for motion in the z axis. Additionally, first probe 110 has θ control components under servo control that allow the receiver 160 affixed to it to be rotated in the x-y plane. Compressed dry air or other gas, for example with a flow rate of 8 SCFM at 80 psi, can be used to operate the robotic heads, and associated apparatuses.

Receiver 160 is mounted with an combined electrostatic and vacuum chuck such as that described in Apparatus for Clamping a Planar Substrate, U.S. patent application Ser. No. 09/095,321, filed Jun. 10, 1998. Vacuum lines, power lines and sensor monitoring lines (not shown) are mounted to the receiver 160 to provide operating resources for the chuck. Where substantial number of lines are to be fixed to the receiver 160, the weight tolerances of the robotics must accommodate the weight, or be modified to accommodate the weight.

Robotic platform 100, is framed by supports 101, which can be used for example to mount barriers such as glass, polycarbonate or acrylic panes (e.g., Plexiglass panes) with which the chamber 102 located above support bench 170 can be isolated from the outside environment. For example, air or inert gas from environmental controller 300 can be used to control the temperature or humidity of the chamber 102. In an illustrative example, the robotic platform 100 has floor dimensions of 135 cm×193 cm, and a height of 150 cm.

Robotic Receiver for Controlling and Operating the Chuck

Figure 3:
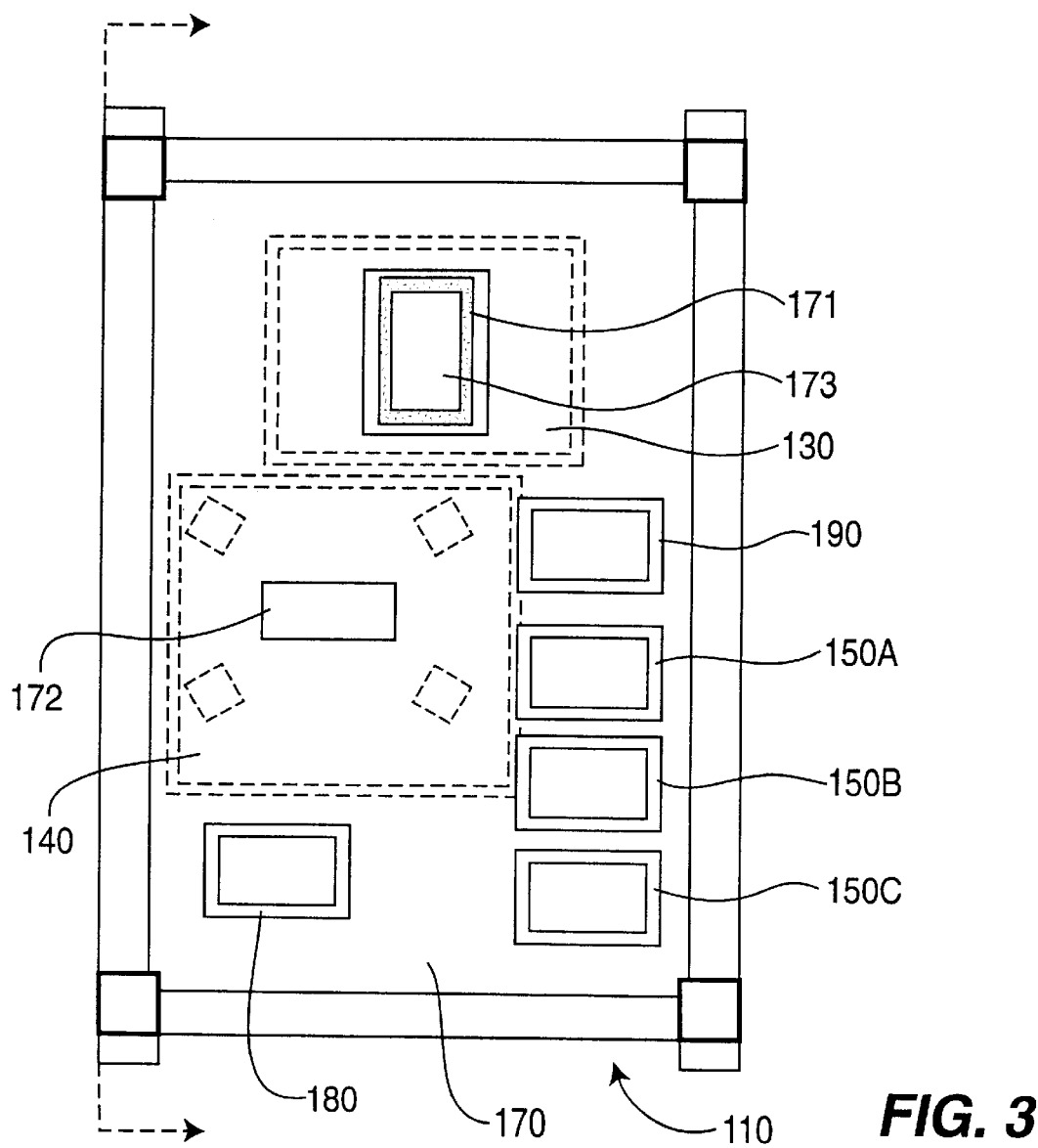
FIG. 3 shows a bench surface in the robotic platform.

Receiver 160 is illustrated as positioned at one of five stations located on bench surface 170, namely at deposition station 130. The stations are substrate input/output station 150 (with three illustrated substations 150A, 150B and 150C), alignment station 190, deposition station 130, dose measurement station 140, and a lamination station 180. The relative locations of these stations on bench surface 170 are illustrated in FIG. 3. FIG. 3 also illustrates deposition gasket 171, deposition opening 173 and measurement window 172 (typically formed of a glass or quartz material suitable to allow the optical measurements described below).

Figure 4B:
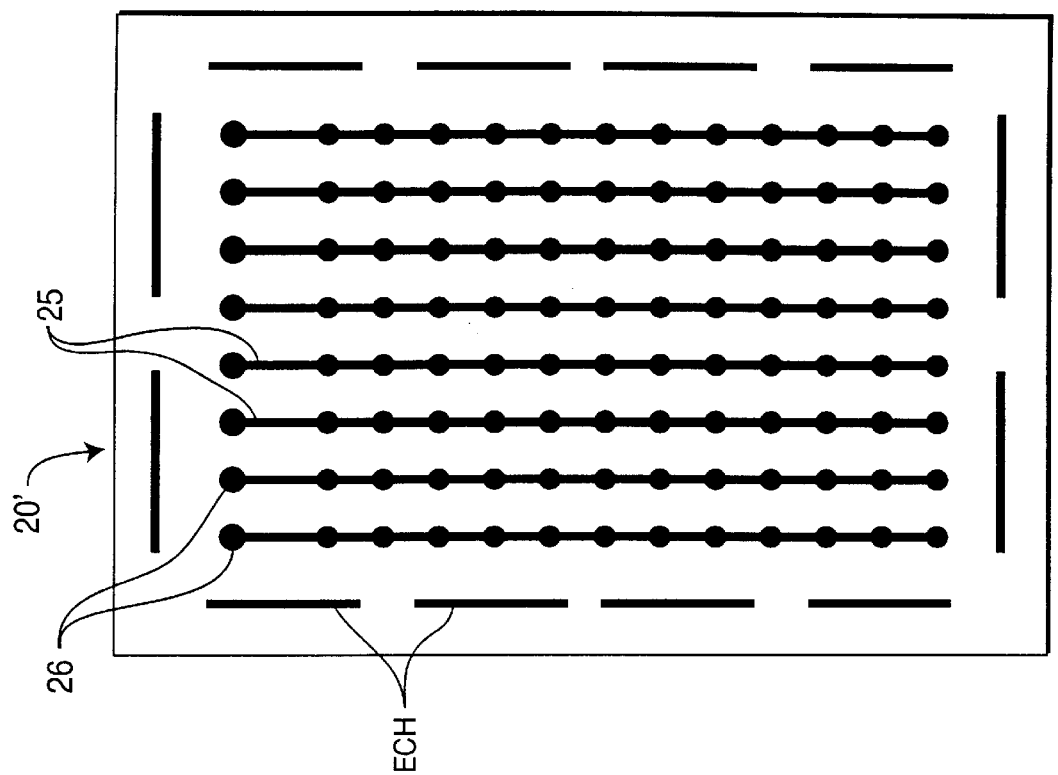
FIGS. 4A–4B show a top and bottom view, respectively, of an electrostatic chuck.
Figure 4A:
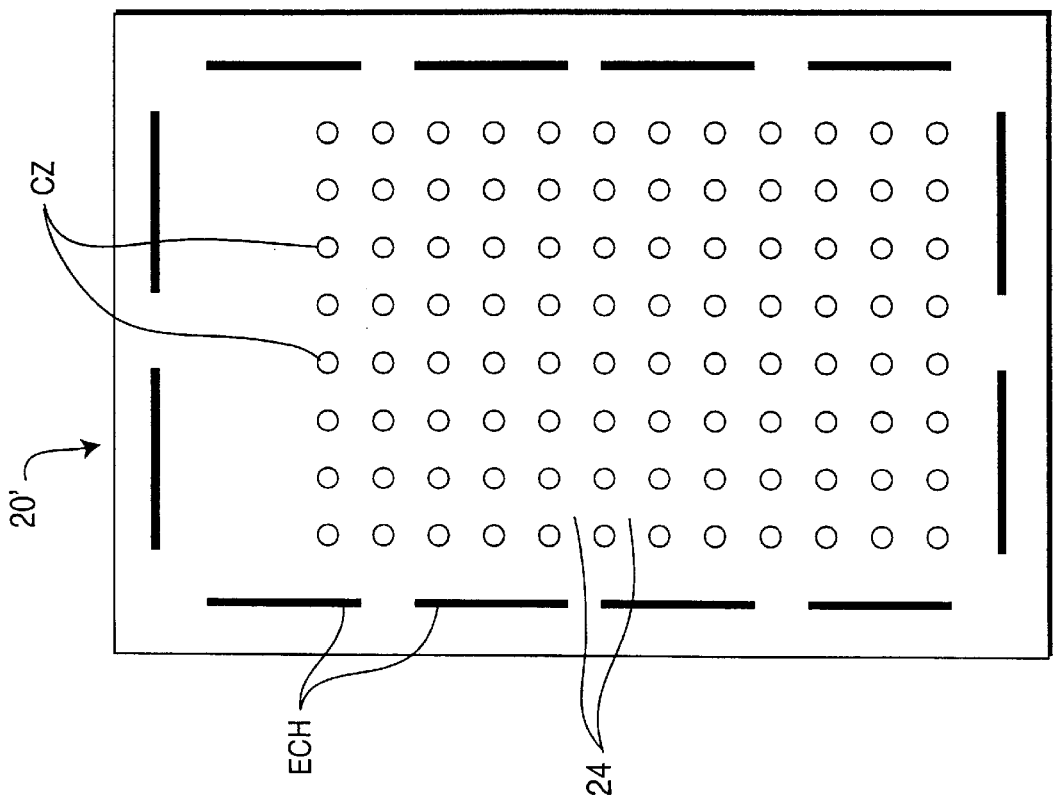

The receiver can be understood with reference to the electrostatic chuck. FIG. 4A shows the upper surface of electrostatic chuck 20' with through holes ECH that are slots and located on the periphery of the electrostatic chuck 20'. The collection zones CZ are located on a surface 24 otherwise composed of a dielectric material Other suitable configurations for electrostatic chuck trough holes ECH are illustrated in U.S. patent application Ser. No. 09/095,321 filed Jun. 10, 1998. FIG. 4B shows a rear surface of the electrostatic chuck 201, which has addressing electrodes 25 through which each row of the grain-attracting electrodes forming the collection zones CZ can be connected to driving electronics. Electrical contact pads 26 provide contact points for connections to voltage sources The illustrative arrangement of addressing electrodes allows each row of grain-attracting electrodes to be separately controlled. Addressing electrodes can be deposited in different patterns to allow different control parameters.

Figure 5A:
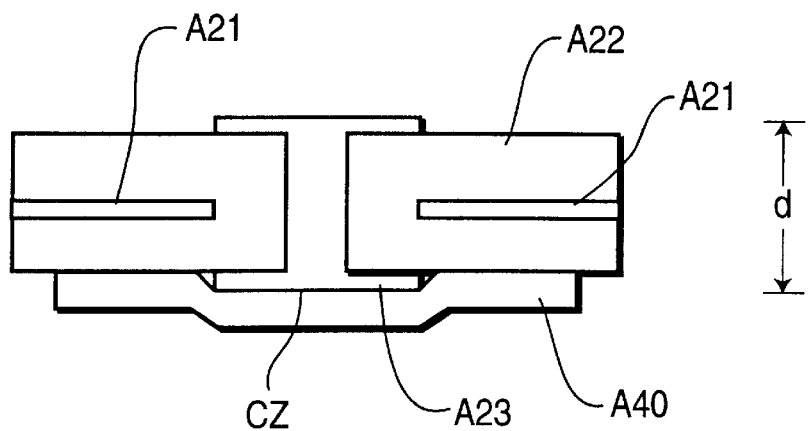
FIGS. 5A–5C show cross-sectional view of localized regions of electrostatic chucks.
Figure 5B:
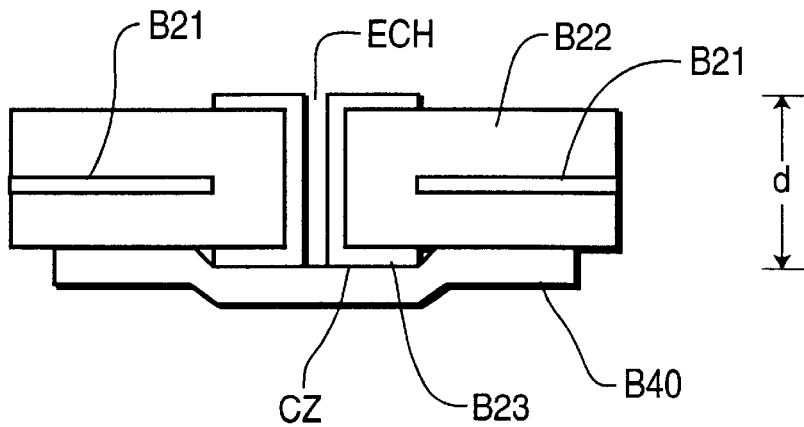
Figure 5C:
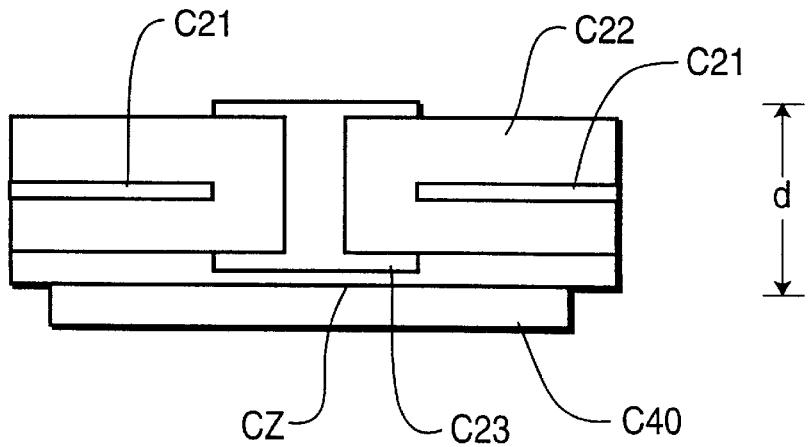

FIGS. 5A–5C illustrate features of electrostatic chucks at a collection zone CZ that can be favorably employed in the invention. In FIG. 5A, the shield electrode A21 (also termed a "ground electrode" based on a preferred bias is layered within a dielectric A22, which dielectric can be, for example, made of KAPTON® (polyimide film, Dupont de Nemours, Wilmington, Del.)(Kapton® can be used as substrate material for Flexible Printed Circuits and can be etched in alkaline solutions, punched and laser drilled, and can be used to form multilayer polyimide film laminates). The grain-attracting electrode A23 projects out at the surface that attracts the planar substrate A40 (which is, for example, 1 mil thick) and can project out at the opposing side where electrical contacts are formed. The width of the electrostatic chuck d can be, for example, 0.01 inches. As such, the electrostatic chuck can be relatively flexible. In the illustration, the planar substrate wraps over the outwardly projecting grain-attracting electrode A23 in a relatively close-fitting manner. The grain-attracting electrodes typically play a role in adhering the planar substrate. A vacuum chuck used in conjunction with the electrostatic chuck can also contribute to attracting the planar substrate. Tight adherence of the planar substrate to the electrostatic chuck increases the reliability of grain deposition at the collection zones.

FIG. 5B illustrates an embodiment where the through holes ECH are formed at the grain-attracting electrodes A23. FIG. 5C illustrates an embodiment where an additional layer of dielectric C22 separates the grain-attracting electrode C23 from the planar substrate C40. The electrostatic chuck provided by the configuration of FIG. 5C can be termed a "Pad Indent Chuck" which is useful, for example for depositions of less than about 2 mg, preferably less than about 100 μg, per collection zone CZ (assuming, for example, a collection zone of 3–6 mm diameter, such as 4 mm diameter). The electrostatic chuck provided by the configuration of FIG. 5A can be termed a "Pad Forward Chuck" which is useful, for example for depositions of more than about 20 μg per collection zone CZ (assuming again, a collection zone of 3–6 mm diameter, such as 4 mm diameter), but which is more useful for higher dose depositions than the Pad Indent Chuck.

Figure 6A:
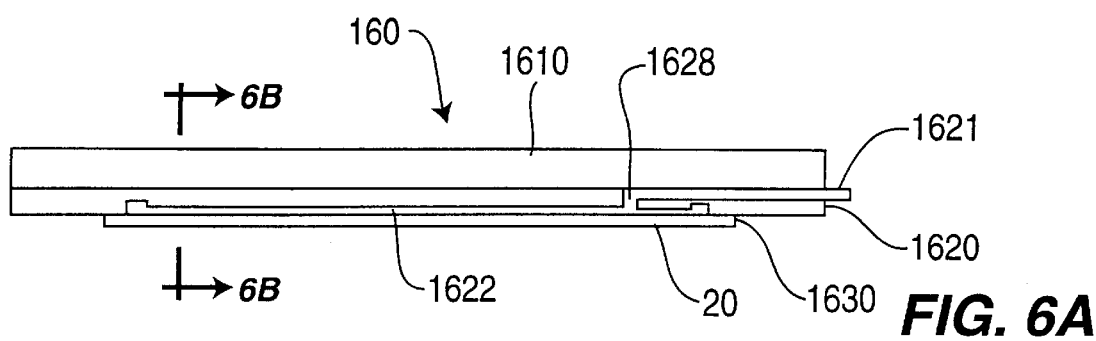
FIG. 6A shows a schematic of a receiver that can carry the electrostatic chuck through various stations in the robotic platform.
Figure 6B:
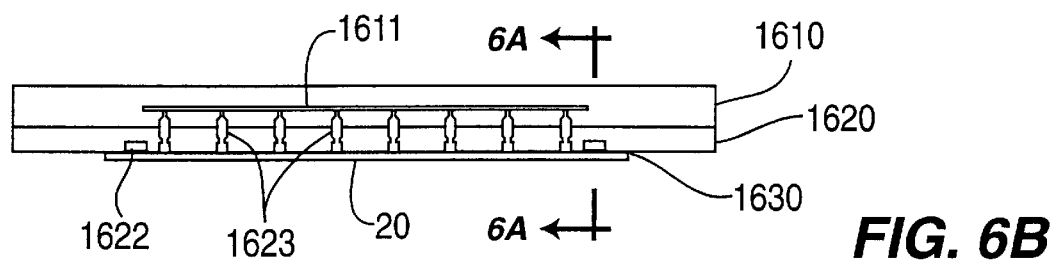
FIG. 6B shows a cross-sectional view of a receiver that indicates how the electrostatic chuck can be electrically connected to circuit boards in the receiver.

Viewed schematically in FIG. 6A, the receiver 160 can be made up of an electronics housing 1610, a vacuum manifold housing 1620, and gasket 1630. The electrostatic chuck can be aligned with the receiver 160 with, for example, locating pins and matching holes. The vacuum manifold has passageways 1622 which convey reduced pressure to the through holes ECH in electrostatic chuck 20. Reduced pressure is applied to the passageways via inlet fitting 1621, and via passageway outlet 1628. Because electrostatic chuck 20 can be quite flexible and delicate, and therefore susceptible to deformation, and because it can be important to deposit grains on a flat surface, a mechanism to couple the grain attracting electrodes to a voltage source without applying significant pressure is preferred. Coupled pins 1623 (see FIG. 6B) provide such a mechanism. Lower pin assemblies of the coupled pins 1623 are inserted through holes in electronics housing 1610, vacuum manifold housing 1620 and gasket 1630, with a conductive adhesive, such as silver epoxy, on the lower part of the lower pin assemblies. The lower pin assemblies are designed with a notch to allow excess adhesive to relocate in the holes. The adhesive adheres the lower pin assemblies to the electrical contact pads 26. The upper parts of the coupled pins are simply standard circuit board pins, which couple with slots on pin connector board 1611.

Figure 6C:
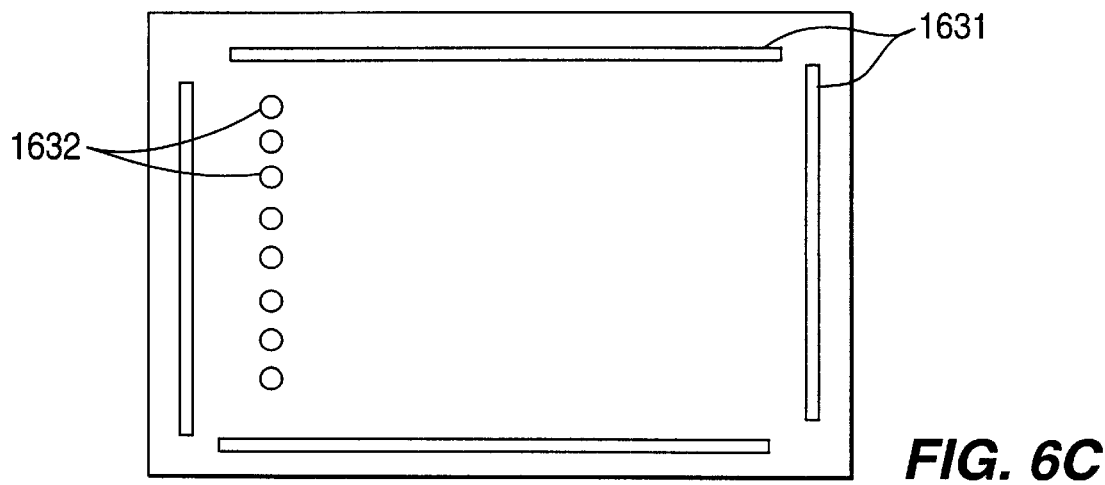
FIG. 6C shows a gasket that intervenes between the electrostatic chuck and the receiver, and enables vacuum to be relayed through holes in the electrostatic chuck.

Gasket 1630 is shown in FIG. 6C, has slot holes 1631 which allow reduced pressure (e.g., vacuum) to be transmitted to the electrostatic chuck through holes ECH. Another set of pin conduit holes 1632 allow the coupled pins 1623 to be inserted through the gasket 1630. The gasket preferably insulates at least about 2,000 or 2,500 V, and in one embodiment is coated on both sides with adhesive. A graphics art paper meeting these requirements, which is of 4 mil thickness and coated on both sides with an aggressive rubber-based adhesive, is available from Cello-Tak, Island Park, N.Y.

Figure 6D:
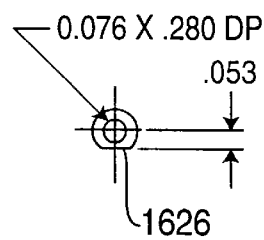
FIGS. 6D–6E focus on a side and top view, respectively, of pins used in connecting the electrostatic chuck to a circuit board.
Figure 6E:
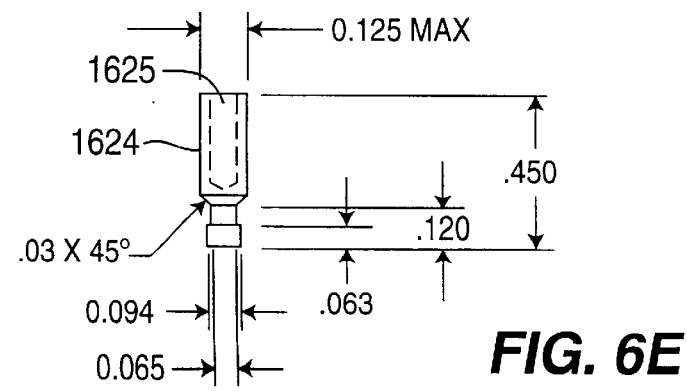

An example of a lower pin assembly 1624 of a coupled pin 1623 is shown in FIG. 6D (side view) and FIG. 6E (top view). Lower pin assembly 1624 has a slot 1625 into which a standard circuit board pin fits, and a notch 1626 that allows excess adhesive to be displaced from the bottom of the cavity into which the coupled pin fits.

The receiver 160 is manufactured from, for example, a durable nonconductive material such as a NORYL® polymer (GE Plastics, Pittsfield, Mass.). NORYL® engineered plastics are modified polyphenylene oxide, or polyphenylene oxide and polyphenylene ether, resins. The modification of these resins involves blending with a second polymer such as polystyrene or polystyrene/butadiene. By varying the blend ratio and other additives, a variety of grades are produced. Unmodified, these polymers are characterized by regular closely spaced ring structures (phenyl groups) in the main molecular chain. This feature along with strong intermolecular attraction causes extreme stiffness and lack of mobility. The strength of the NORYL®-based structure provides a firm support for maintaining a flat surface collection zone CZ containing surface of the electrostatic chuck 20, while the low weight reduces any burden on the robotic heads (110 or 120). The surface of the receiver .160 on which the electrostatic chuck 20 is mounted can be machined flat, for example to ±1 mil.

Figure 7A:
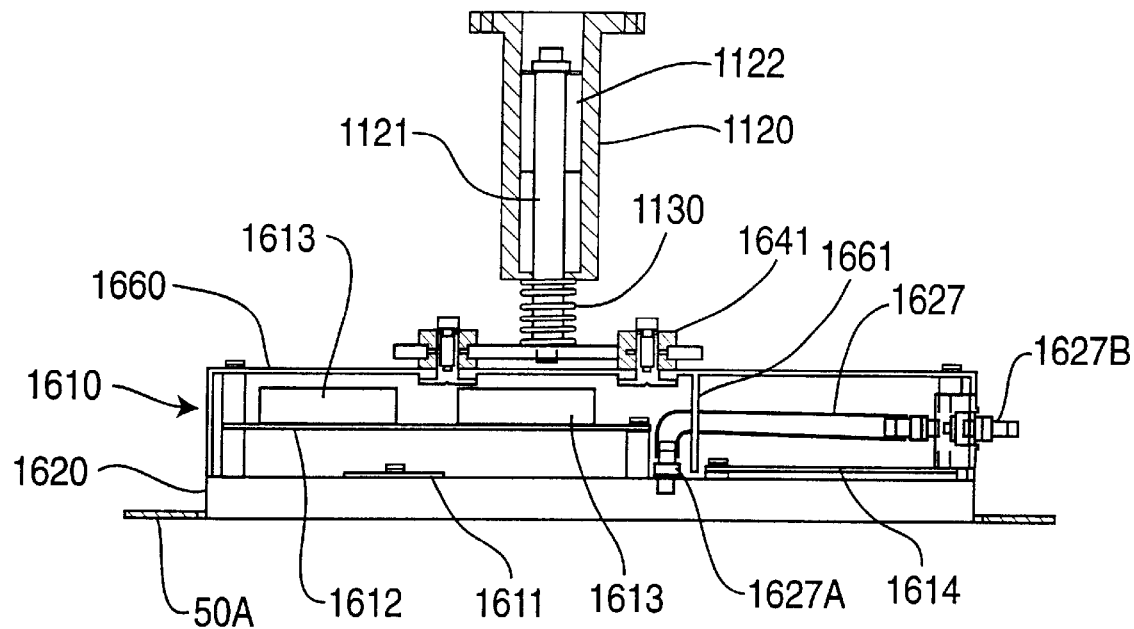
FIG. 7A shows a cut-away view of a receiver, which cut-away is indicated in the side view of FIG. 7B.

Referring to FIG. 7A, the receiver 160 is mounted to first robotic head 110 via bearing housing 1120. Bearing housing 1120 contains spline shaft 1121 and spline shaft bearings 1122. Bearing housing 1120 allows the receiver to be moved up and down in the z-axis. Bearing housing 1120 couples to floating bolt assembly 1640 via spring-loaded coupling 1130. Floating bolt assembly 1640 mounts to receiver cover 1660 via visco-elastic isolation bushings 1641 (made, for example, of the isolation damping material sold as Sorbothane® by Sorbothane, Inc., Kent, Ohio). The visco-elastic isolation bushings 1641 allow the receiver 160 to be moved slightly when receiver locating pins 1650 are inserted into alignment socket holes located on bench surface 170. In this way, the locating accuracy of the robotic head (which is, for example, repeatable to ±2 mil) can be increased when the substrate is presented for dry deposition at deposition station 130 (for example, to ±0.5 mil). The floating bolt assembly 1640 allows the receiver 160 to comply with alignment actions acting in a direction in an x, y or z axis.

Figure 7B:
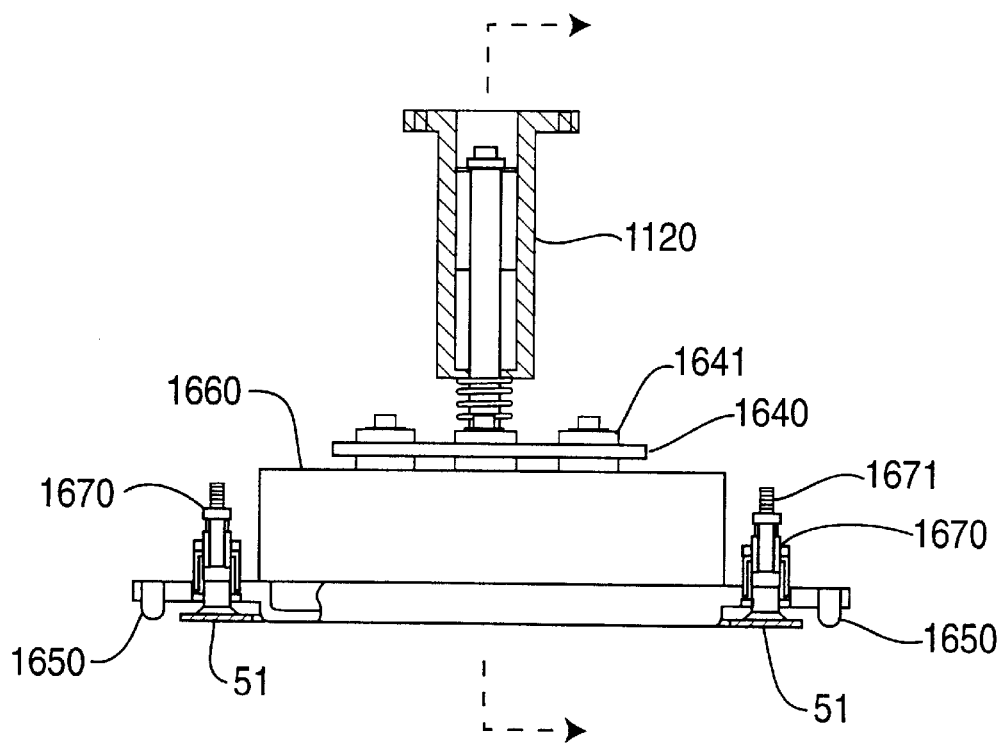

FIG. 7A shows the cut-away indicated in FIG. 7B. Further indicated in FIG. 7A are pin connector board 1611, high voltage board 1612, high voltage chip areas 1613 and embedded processor board 1614 (particularly optional, since processing can be conducted at robotic platform 100). High voltage barrier wall 1661 keeps the high voltage areas of the receiver 160 isolated. Also shown is vacuum tubing 1627, first tubing connector 1627A for connecting vacuum tubing 1627 to inlet fitting 1621, and second tubing connector 1627B for connecting to an external vacuum source. Substrate frame 50A, on which is mounted a planar substrate, is shown adhered to the underside of the receiver 160. As discussed further below, the frame provides an optional means of assuring alignment with the post-deposition detection device. The substrate frame can be made of a suitably strong material which is preferably light weight, such as, for example aluminium. The frame is, for example, 200 mm by 300 mm, with sides having 12.7 mm width. FIG. 7B shows vacuum cup receiving fixtures 51 on the substrate frame 50A, height adjustable vacuum cups 1670, and vacuum hose fittings 1671.

Figure 8A:
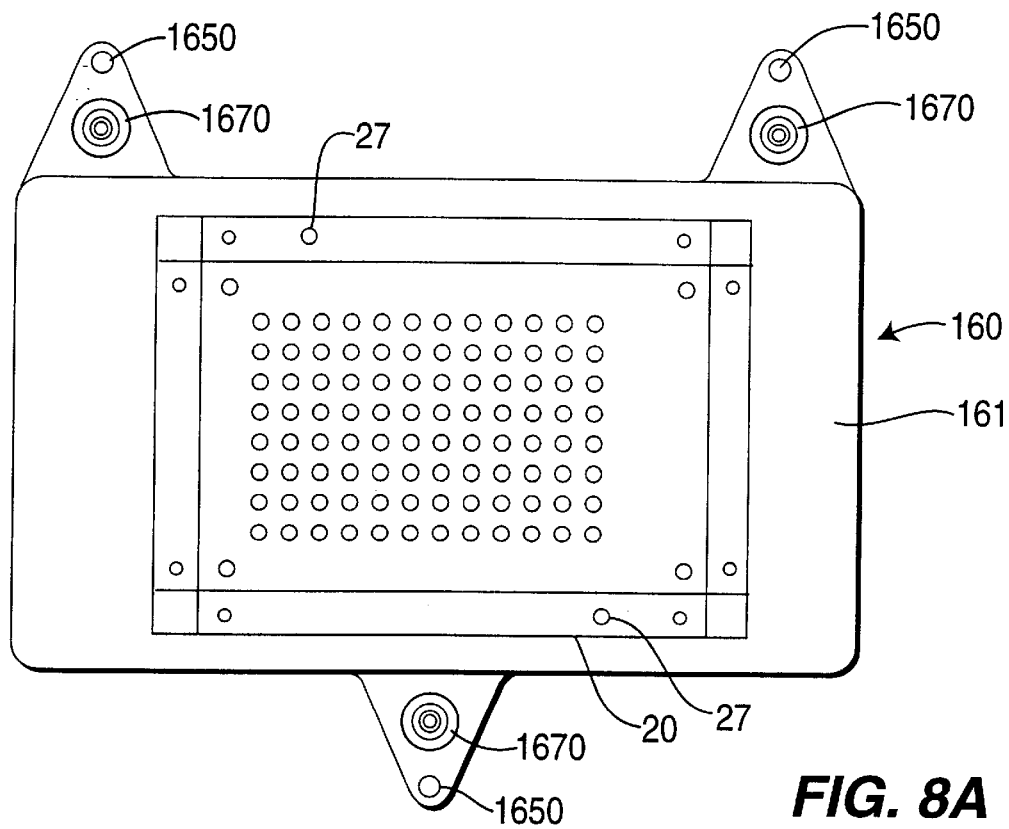
Figure 8B:
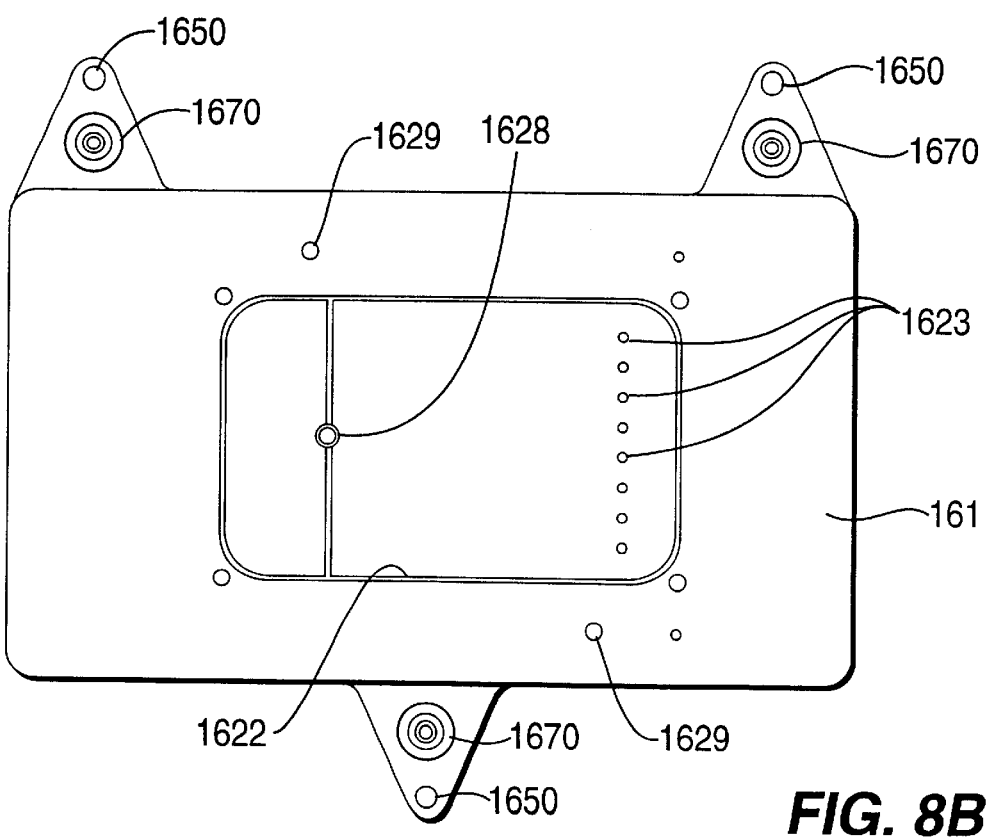
FIG. 8B shows the underside without the electrostatic chuck.

FIG. 8A shows electrostatic chuck 20 adhered to underside 161 of receiver 160. Electrostatic chuck 20 has alignment mechanisms 27. FIG. 8B shows underside 161 without an adhered electrostatic chuck 20. This view shows the passageways 1622 and passageway outlet 1628, along with pin conduits 1623A. Further shown are alignment mechanisms 1629, which can be, for example, alignment pins or alignment pin receptacles.

Figure 9A:
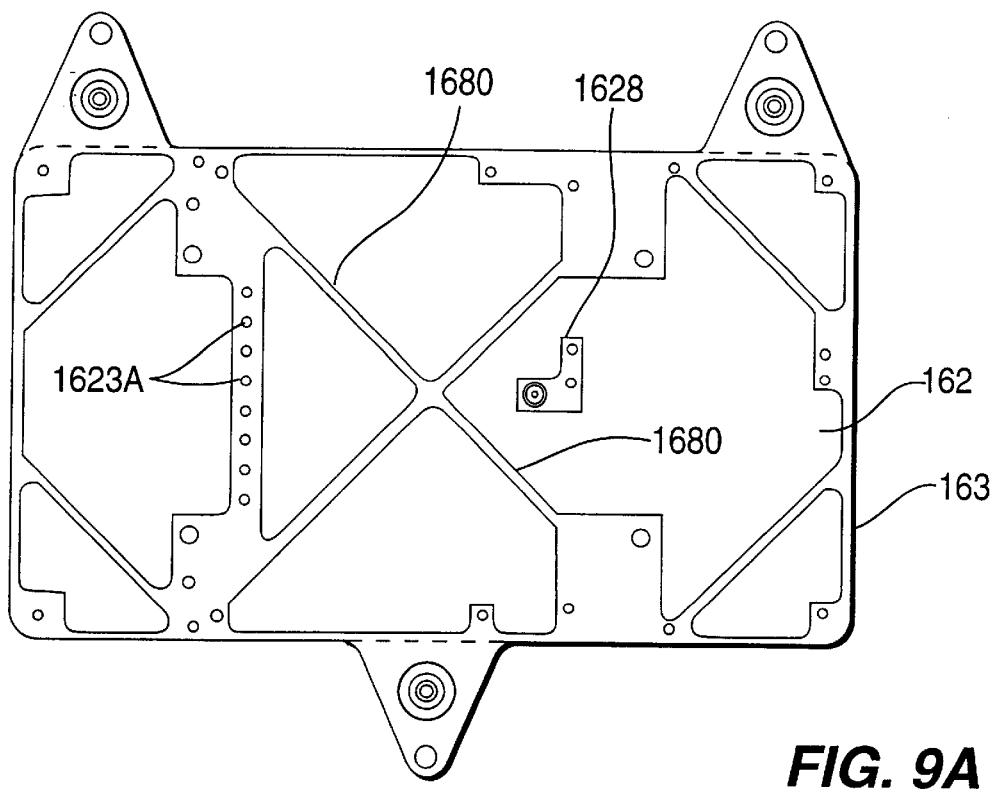
FIG. 9A shows a platform in a receiver which, as illustrated in FIG. 9B, supports certain circuit boards that can be mounted in the receiver.
Figure 9B:
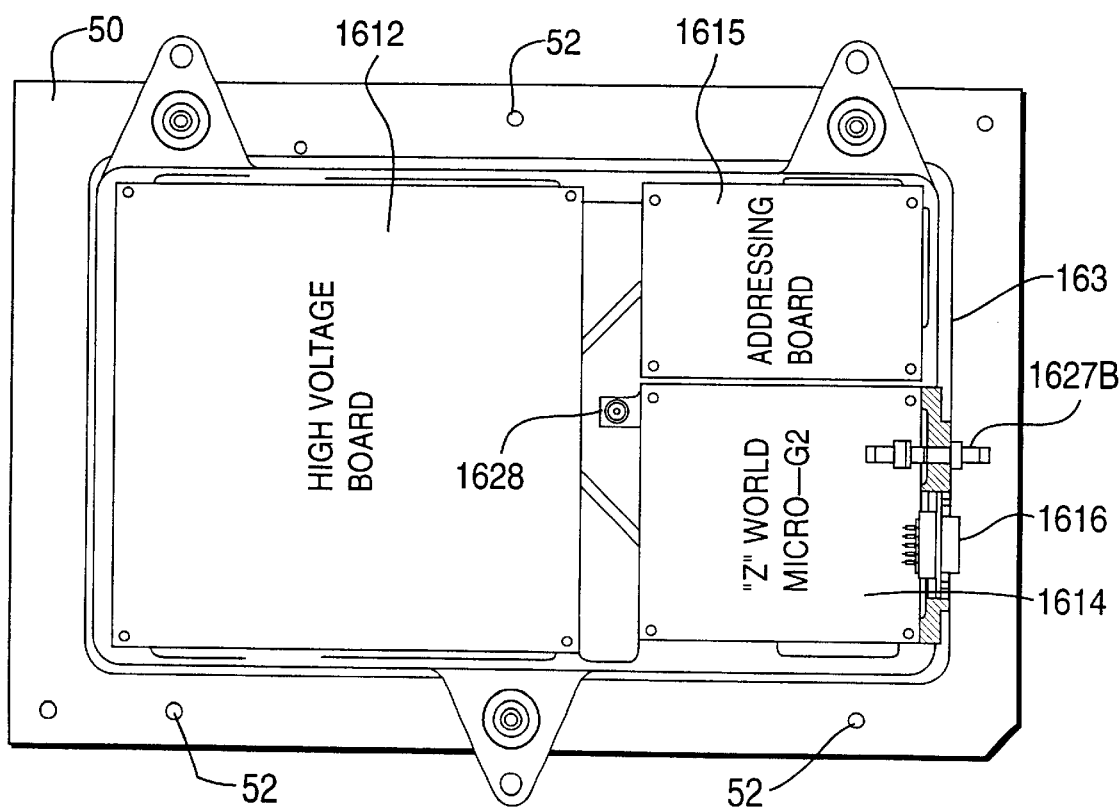

FIG. 9A shows the upper side 162 of receiver platform 163, the underside of which is underside 161. Receiver platform 163 has moldings forming reinforcing braces 1680, passageway outlet 1628 and pin conduits 1623A. As illustrated in FIG. 9B, the moldings on upper side 162 support embedded processor board 1614, addressing board 1615 and high voltage board 1612 (i.e., bias generation board). Electrical communication to electronics located off the receiver can be done through port 1616.

Electronic control can be integrated in the dry powder deposition apparatus, typically with equipment located at the electronic cabinet. In the receiver 160, embedded processor board 1614 can function as a communications board, that receives commands from a central control computer, such as central processor unit 410, and relays these commands to the addressing board 1615. Also, in some embodiments, embedded processor board 1614 receives data from sensors positioned on or adjacent to the electrostatic chuck (described further below), and interprets locally any adjustments to voltages applied to the grain-attracting electrodes 23 that are appropriate in light of this data. The addressing board 1615, in turn, after receiving signals from the on-board processor board 1614, sends bias control signals, which can be, for example, DC or AC signals, for controlling the voltage at the grain-attracting electrodes 23, or, for example, to separate columns or rows of grain-attracting electrodes, or to individual grain-attracting electrodes. Such adjustment can be made, for example, where sensors, or data from the dose measurement station 140 based on a previous deposition, indicate that an uneven distribution of grain deposition amounts is occurring, so that it may be advantageous to increase or decrease voltages at collection zones CZ accordingly. Note that the electrostatic chuck illustrated in FIGS. 4A and 4B has addressing electrodes 25 that allow control of individual rows of grain-attracting electrodes. Control patterns that control regions or individual collection zones CZ can also be used. The addressing board 1615 preferably has multiple channels of synchronized output (e.g., square wave or DC). The signals sent to the addressing board can be encoded, for instance with a pattern of square wave voltage pulses of varying magnitudes, to identify the grain-attracting electrodes 23 (or group of electrodes) together with the appropriate voltage to be applied. The bias control signals are sent via the high voltage board 1611, which has multiple channels of high voltage converters (transformers or HV DC-to-DC converters) for creating the voltages, such as 200 V or 2,500 V or 3,000 V (of either polarity), for operating the grain-attracting electrodes. By forming the higher voltages within the receiver 160, these high voltages can be isolated from other systems.

As will be discussed further below, the central processor unit 410 can receive performance input from multiple sources. This input provides data on the rate of particle flux into and through the deposition engine (made up of grain feed apparatus 200 and deposition station deposition station 130), how evenly particles are being deposited at the electrostatic chuck 20, as for example determined from on-board sensors, how well previous depositions have met standards, and the like. With this information, various parameters can be adjusted, including the voltages at various locations on the electrostatic chuck 20, to improve performance. The on-board electronics discussed above provide a means for these adjustments-on-the-fly to be conveyed to grain-attracting electrodes 23.

Charge Sensor

The charge sensor, which is an on-the-receiver device for monitoring the amount of grains being deposited, is described in detail in copending "AC Waveforms for Bead Manipulating Chucks," U.S. application Ser. No. 09/095,425, filed Jun. 10, 1998. This copending application describes the use of pulsed (AC) electrical potential waveforms for biasing an electrostatic chuck to collect grains, such as on a substrate. This form of biasing overcomes the problem of collecting grains on a conductive substrate, where the grain-attracting field can decay rapidly after any given application of a bias potential to the electrostatic chuck.

The use of AC bias waveforms for the grain-attracting electrode also solves another long-standing problem during deposition sensing. In deposition sensing, one or more bead collection zones are closely monitored for grain accumulation, so as to allow regulation of the grain deposition process, to produce for example precise dosages. This monitoring can be done optically or by measuring accumulated charge using an "on-board" charge sensor at a sensor-associated bead collection zone, which can be correlated to actual charged grain deposition by empirical data collection. In dry powder deposition, for example, dose monitoring is often a very difficult task, particularly for dosages below one milligram.

The difficulty is not that measuring devices are not available—modern solid state devices, although expensive, can make measurements so precise that noise levels are on the order of the voltage generated by the charge of a few hundred electrons. Rather, the difficulty lies with various practical and environmental factors that can deteriorate charge sensing sensitivity by two or three orders of magnitude. For quasi-static DC biased bead transporter chucks, on-board charge sensing is particularly difficult. Data obtained by depositing on a polypropylene film substrate with different potentials indicates that the deposited dose is linearly related to the bias potential if that potential is above a certain threshold potential. Data indicates that threshold potential is about 100–200 volts DC, at least for certain transporter chucks.

Figure 20:
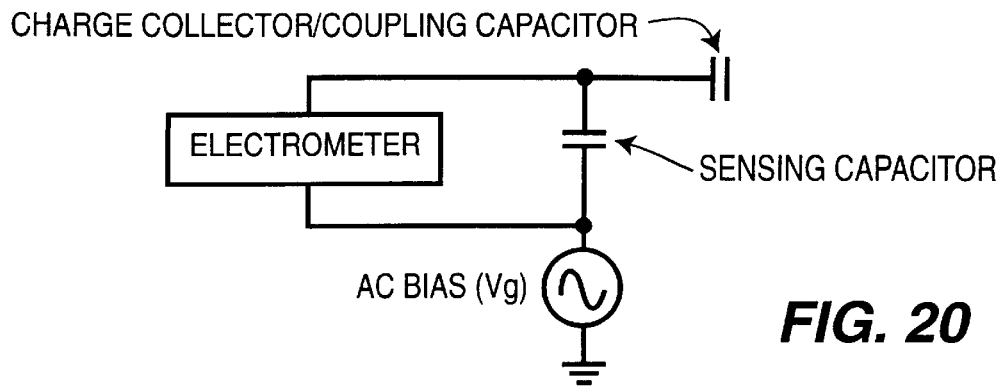
FIG. 20 shows one possible equivalent circuit diagram that provides AC biased charge and deposition sensing for at least one collection zone.
Figure 21:
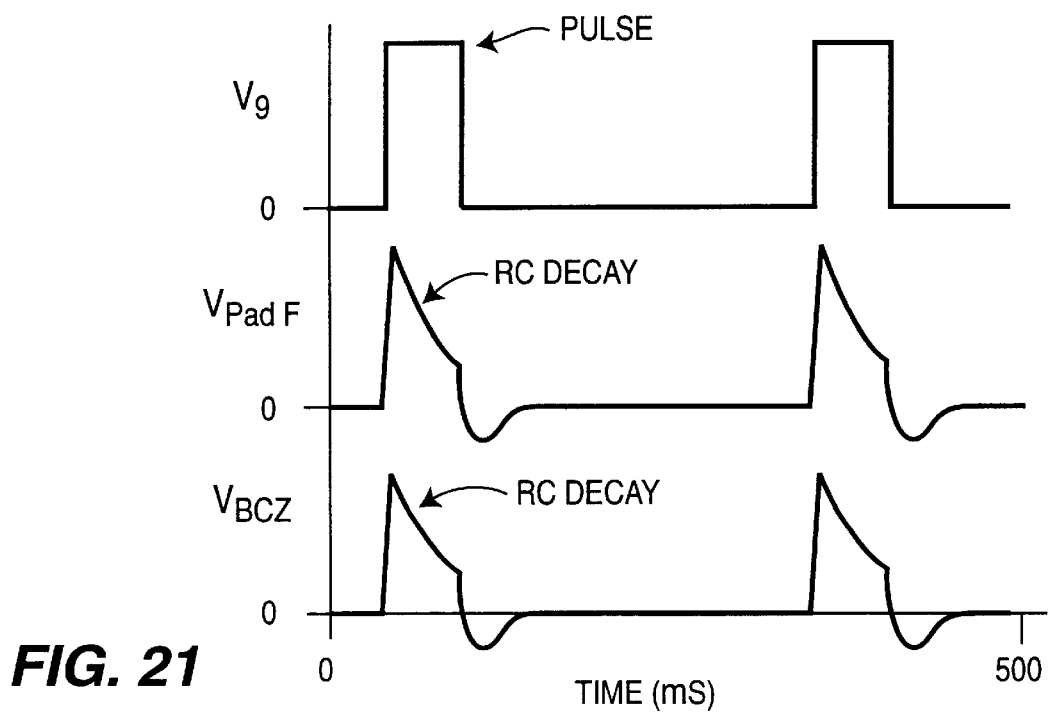
FIG. 21 shows three Cartesian graphical waveforms representing applied and resultant voltages in the bead transporter chuck as a function of time, where a low-resistivity substrate is applied thereto, and using AC waveforms biasing.

FIG. 20 shows one possible equivalent circuit diagram that provides AC biased charge and deposition sensing for at least one of bead collection zones, which zone has a floating pad electrode (not shown). The floating pad electrode is an isolated conductor which is designed to be capacitively coupled to a grain-attracting electrode, such that the bias to the grain-attracting electrode indirectly creates a grain-attracting field emanating from the floating pad electrode. One or more collection zones are typically dedicated solely for sensing or are in general use, but closely monitored. By measuring the lowering of the attraction potential $V_{CZ}$ that occurs as charged beads deposit on the bead collection zone, a measure of deposited charge can be obtained, and by knowing the average charge/mass ratio q/m of the deposited grains (e.g., beads or powder), the accumulated grain deposition mass can be measured. One can measure $V_{CZ}$ directly across a charge collector electrode, but it is often preferable to measure the potential across a coupling capacitor, such as the floating pad electrode discussed above. The coupling capacitor as embodied by floating pad electrode above will provide reasonably high fidelity reproduction of the potential at the collection zone CZ on the bead contact surface, and in FIG. 21 the waveforms for $V_{CZ}$ and $V_{Pad}$ reflect this. In either case, whether a charge collector or charge coupling capacitor is used, they may both be considered charge sensing electrodes. In the equivalent circuit of FIG. 20, the charge collector/coupling capacitor is electrically connected to a separate sensing capacitor. The voltage generated across the sensing capacitor can be a reliable indicator of the potential $V_{CZ}$, and one simply measures the voltage across the sensing capacitor with an electrometer, such as a Keithley model no. 614, 6512, 617, 642, 6512, or 6517A electrometer, as shown schematically in the figure. Generally the coupling capacitor is any electrode that is capacitively coupled to a bead collection zone on the bead contact surface.

A problem is that DC biasing can cause a steady drift in the reading of the potential across the sensing capacitor. This drift comes from many sources, mostly from natural leakage across the dielectric material in the sensing capacitor, and because of charge leakage in the substrate or grain composition on the accumulated on the chuck. Drift can also be induced by noise factors such as shot noise, Johnson (1/f) white noise, thermal noise, Galvanic noise, triboelectric noise, piezoelectric noise, amplifier noise, and electromagnetically induced noise. See ref: *The Art of Electronics*, by Paul Horowitz, Winfield Hill, 2nd Edition, Cambridge University Press, © 1989.

If this drift is too large compared to the actual charge collected at the bead collection zone, the accuracy of the charge sensor as a dose or deposition measurement tool can be unacceptably low. Using AC biased waveforms as taught here, however, minimizes the creation of drift, in a manner similar to that which can be used for avoiding the "drift" of charge dissipation on the bead collection zone, allowing precise measurement of charge collected. As shown on the figure, an AC bias source is shown, and may simply be the same source as discussed above, with the AC bias potential simply applied or administered via the grain-attracting electrode. This will in turn electrically couple to the floating pad electrode or to the bead collection zone itself, if one elects to connect it directly to the sensing capacitor as shown.

For example, if the sensing capacitor is chosen to be 0.1 $\mu$F, and the q/m of the powder is 10 $\mu$C/g, a 100 mV signal change on the charge collector/coupling capacitor corresponds to 1 mg of powder deposited on the bead collection zone. If, say, the linear correlation factor is 3, then 1 mg of powder on the sensor corresponds to 3 mg of powder in the actual deposition dose, then a 99 $\mu$g actual dose will have a detectable potential change of 3.3 mV. With a 5% error tolerance, the corresponding background unpredictable noise contribution cannot exceed 160 $\mu$V. This is achievable with careful shielding and grounding design. Preferably the charge collector is integrated with the chuck design to assure a consistent correlation.

Figure 22:
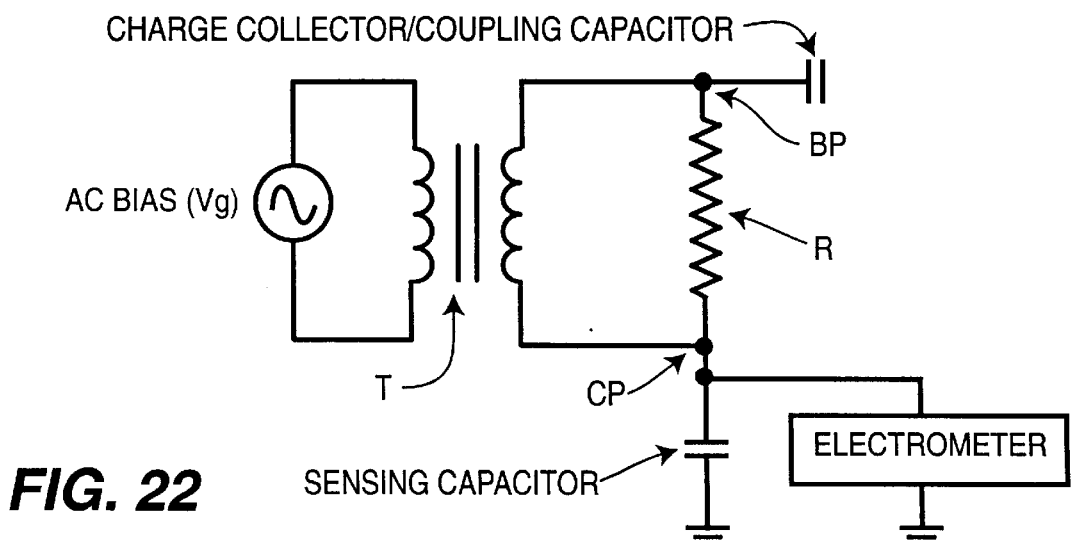
FIG. 22 shows another possible equivalent circuit diagram that provides AC biased charge and deposition sensing for at least one collection zone.

Referring now to FIG. 22, another possible equivalent circuit diagram that provides AC biased charge and deposition sensing is shown. This arrangement further reduces noise by separating the AC bias source from the electrometer, the sensing capacitor or the charge collector/coupling capacitor, all components whose sensitivity to noise is critical. As shown in the figure, the AC bias source is connected to the primary of a transformer T. In this manner, only the periodic magnetic field generated by $V_9$, (not $V_9$ itself) is introduced into the sensitive components on the right side of the figure. The secondary winding of transformer T is connected across a stabilizing bleed resistor R, with one pole, biasing pole BP connected to the charge collector/coupling capacitor, and the other pole, the sensing capacitor pole CP connected to the sensing capacitor. To further reduce noise, the sensing capacitor is connected to ground. The electrometer can then measure the voltage change on the sensing capacitor with respect to ground, as shown. These two grounding points can be combined to reduce electromagnetic noise further. The transformer can be a step-up transformer as discussed above so that complex AC bias waveforms supplied here and to the grain-attracting electrode can be generated inexpensively. For example, the step-up ratio can be 50. This arrangement greatly reduces drift and make accumulated charge sensing more accurate, where previously the coupling current of 100 pico-Amperes or less made drift and noise a real problem.

If desired, transformer can be an isolation transformer, where the primary and secondary windings are separated by a Faraday cage. This can prevent coupling between the primary and secondary windings, where the primary winding acts as one capacitor plate, and the secondary as the other capacitor plate.

With this improved signal to drift ratio the amount of charge sensed can decrease substantially. Measurements can now be made using a 1000 picoF capacitor as the sensing capacitor instead of the 0.1 $\mu$F value used previously. Also, the AC bias source as shown in FIGS. 20 and 22 can be separate from the AC waveform bias $V_9$ on the chuck, by delivering a separate AC bias to the charge collector/coupling capacitor directly, via a dedicated wire, electrode, bus, etc. This separate AC bias can be frequency matched or detuned with respect to $V_9$ to insure consistent correlation of the behavior of the charge collector/coupling capacitor to actual depositions.

Overall, too, these techniques allow $V_9$ biasing with voltage peaks much higher than previously possible. Using 8000 molecular weight polyethylene glycol as a substrate, bias peaks of 2 kV have been used. It is important also to keep in mind that any kind of bead transporter chuck can be used, including those that operate with bias electrodes directly exposed to the bead contact surface (such as illustrated in FIG. 5).

Substrate input/output station and alignment station

Figure 14:
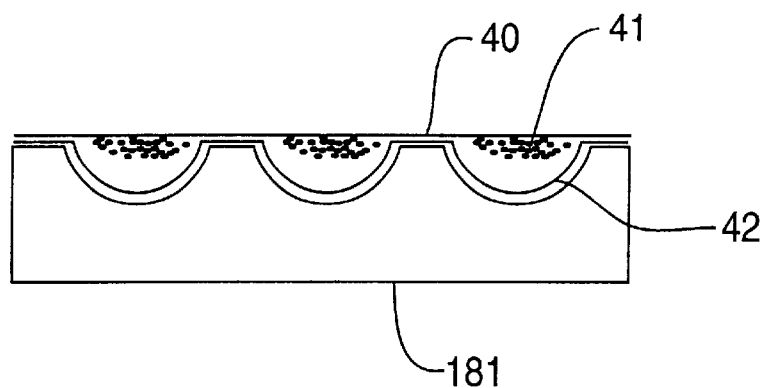
FIG. 14 shows a fragment of a lamination support block.

The substrate is typically a flexible planar substrate, which has, for example, a thickness of about 1 mil. Suitable substrate materials include polyvinylacetate films such as are available from Polymer Films, Inc., (Rockville, Conn. [moving to West Haven, Conn.]), Chris Craft, (Gary, Ind.), Aquafilm, (Winston-Salem, N.C.), Idroplast S.p.A. (Montecatini Terme (PT), Italy), AlCello Chemical Co., Ltd. (Toyohashi, Japan), or Soltec (Paris, France). Other suitable substrates include hydroxypropylmethylcellulose and polyethylene oxide films. The substrates, in one illustrative embodiment, are mounted in substrate frames 50, which are stored in the robotic platform 100 at input/output station 150. Also stored at input/output station 150 are covering substrates mounted on second frames 50B. These covering substrates can be shaped to have indentations at locations corresponding to the coated regions to which the grain-attracting electrodes will attract grains to the substrate 40. For example, FIG. 14 shows a fragment of a lamination support block 181 on which the indented covering substrate 42 covers grains 41 which are deposited on substrate 40. First input/output substation 150A can contain frames 50A on which are mounted substrates 40. Second input/output substation 150B can contain second frames 50B on which are mounted covering substrates 42. Third input/output substation 150B can contain interlocked frames 50 containing the bonded substrate 40 and covering substrates 42 which are produced by the dry powder deposition apparatus.

First robotic head 110 picks up a frame 50A containing a substrate 40 at input/output station 150, and then deliver it to alignment station 190, where the frame 50A is released so that alignment mechanisms 52 pair up with (e.g., as in male/female sockets) corresponding alignment mechanisms at the alignment station 190. The robotic head 110 then again picks up the frame 50A, this time with the system assured that the frame is properly aligned with the localization of the robotic head, so that the frame localized to within the accuracy of the robotic head 110 (e.g., ±2 mil). Alignment station 190 also has a visco-elastic pad (not shown), such as a foam rubber pad, onto which the substrate 40 is pressed to remove an air pockets between the substrate 40 and the receiver 160. With the substrate 40 pressed against the pad, the substrate-adhering vacuum of the receiver 160 is activated, and the grain-attracting electrodes can also be activated (where the grain attracting electrodes typically also attract the substrate).

The alignment station provides at least two benefits. When a substrate frame 50 is stacked at an input/output station a robotic head comes down with a clamping feature such as vacuum cups 1670, the stacking creates imprecision in the alignment between the substrate frame and the robotic head. By releasing the frame so that a fixed alignment mechanism corrects the orientation of the frame, the robotic head can pick up the frame so that the deposition apparatus controller has confidence of the position of the frame to the accuracy of its placement of the robotic head. Also, the visco-elastic pad helps initiate intimate contact between the electrostatic chuck and the planar substrate.

Second robotic head 120 can pick up a second frame 50B containing a covering substrate 42 and use alignment station 190 to confirm localization of the second frame 50B. The second robotic head 120 can then be moved to deposit frame 50B so that the covering substrate sits on lamination support block 181 as illustrated in FIG. 14.

An alignment mechanism is thus described in part for the illustrated embodiment where substrates are processed in a piece-wise fashion. Framing and alignment concepts are further described below with reference to the deposition station 170 and the dose measurement station 140, where it can be particularly important that measurements are made at the same positions as depositions were made. Alignment issues can also be important in continuous processing contexts, where similar concepts can be employed. For instance, if the substrate is deployed on a tape, frames can be periodically locked to the tape as it is processed through portions of the dry powder deposition apparatus where alignment issues are particularly important. So that there is adjustment room, a small amount of loosely fitting tape can be employed between the locked frames, thereby allowing the spacing between the frames to be adjusted based on alignment considerations.

Deposition Engine

After alignment, the first robotic head 110 can move the frame 50A containing a substrate 40 to deposition station 130, which forms a part of a deposition engine. Alternatively, the first robotic head 110 can move the substrate 40 to the dose measurement station 140 so that baseline optical data can be recorded prior to deposition, and then the robotic head can move to the deposition station 130. Note that to align the frame 50 with deposition opening 173, the robotic head is rotated 90°. Receiver locating pins 1650 are used to closely establish the alignment of the receiver 160 with the deposition opening 173.

Figure 10:
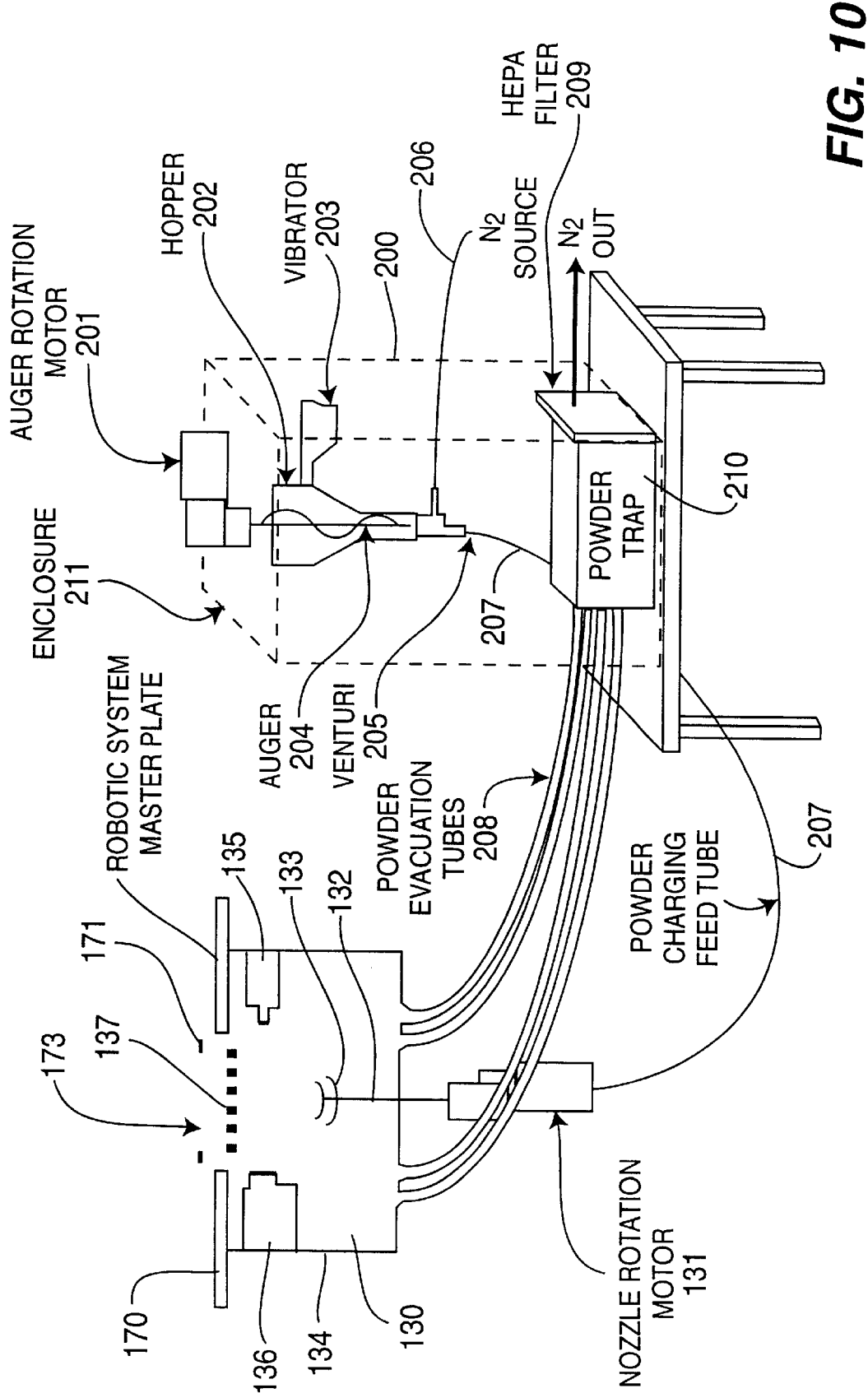
FIG. 10 illustrates a deposition engine.

A deposition engine is illustrated in FIG. 10. Substantially within enclosure 211, the grain feed apparatus 200 is made up of auger rotation motor 201, hopper 202, vibrator 203, auger 204, Venturi feeder valve 205, clean gas source 206, which feeds into Venturi feeder valve 205, powder charging feed tube 207, powder evacuation tubes 208, powder trap 210, and HEPA filter 209 (HEPA, High Efficiency Particulate Air, 99.97 percent efficiency in capturing 0.3-micron particles). The vibrator is illustrated as acting on the hopper 202, but can favorably be applied to a shaft driving a mechanical grain-moving appliance such as the auger 204. The powder charging feed tube 207 feeds charged grains into nozzle 132, which has a rotating baffle 133 which serves to increase the uniformity of the grain cloud, sometimes referred to as a powder cloud, that reaches the collection zones CZ on an electrostatic chuck positioned on the gasket 171 framing deposition opening 173. Nozzle rotation motor 131 drives the rotation of rotating baffle 133. The nozzle is in deposition station 130, which is enclosed by deposition station enclosure 134, which can be for example an acrylic enclosure.

Grains fed through nozzle 132 towards the collection zones CZ (target) on an electrostatic chuck framed by deposition gasket 171, and through control grill 137. Control grill 137 is favorably located at a distance d for example about 0.5 inch to about 10 inch, below the target, and biased at about 500V per ½ inch of distance $d_{grill}$ at the polarity intended for the grains. Control grill 137 thus serves to collimate the powder cloud and attract grains having the wrong charge. Control grill 137 can be, for example, a series of parallel electrical wires (which can be formed from switchbacks of one wire) or a grid of wires, having for example a separation of about 5 mm to about 15 mm. The rate of powder cloud flux can be monitored by measuring light attenuation between light emitter 135 (which is, for example, a laser emitter) and light detector 136. This value can be transmitted to central electronic processor 410.

An illustrative nozzle 132 with rotating baffle 134 is shown in more detail in FIG. 11. Grains are fed through the nozzle 132 with, for example, a gas at about 20 psi and about 2.5 liters per minute. The gas is preferably substantially free of water, oil and other impurities, and is preferably a chemically inert gas such as nitrogen or helium. The baffle serves to increase the uniformity of the powder cloud at the target, with the baffle favorably being located, for example, about ¼ inch to about ½ inch above the outlet of the powder charging feed tube 207, and having larger cross-section than the outlet of the powder charging feed tube 207, such as ½ inch cross-section where a ¼ inch powder charging feed tube 207 is used. Rotating the baffle, for example at from about 5 to about 25 rotations per minute, increases the uniformity of the powder cloud reaching the target.

Figure 11A:
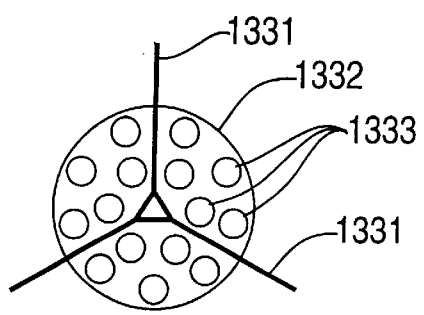
FIG. 11 shows a nozzle with rotating baffle used in the deposition engine.
Figure 11B:
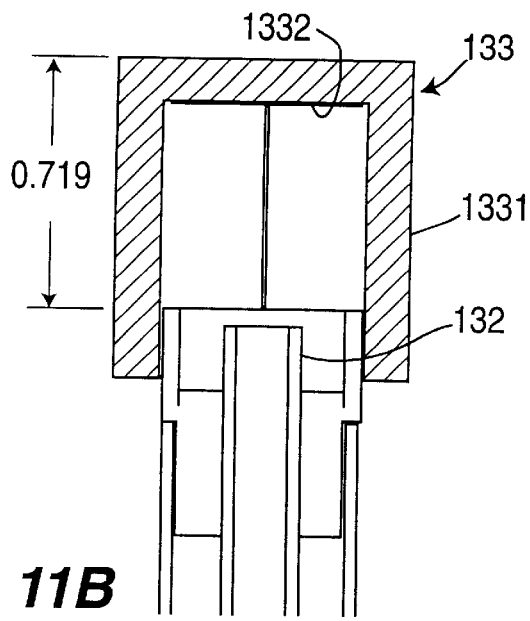

FIGS. 11A and 11B show a top and side view, respectively, of a rotating baffle 133. The rotating baffle 133 is supported by baffle supports 1331, on which rests baffle disk 1332, in which are found baffle outlets 1333. The illustrated scale is in inches.

Returning to the auger 204, the auger is turned, for example, at about 10 to about 80 rotations per minute to feed grains into Venturi feeder valve 205. Avoiding compaction of the grains was a design issue for the Venturi feeder valve 205. A modified Venturi feeder valve with a Venturi well that delivered grains in a substantially straight line from the auger feed to the powder charging feed tube was incorporated, thereby avoiding the compaction seen when the grains fell to the bottom of the Venturi well. The Venturi well should be accessible, for example, by an unscrewing action, so that it can be periodically vacuumed. The Venturi feeder valve 205 acts, when gas pressure is applied, to pull grains from the auger 204 and the gas feed (for example nitrogen) acts to push the grains through the powder charging feed tube 207. Suitable Venturis can be obtained from, for example, Vaccon Company, Inc. through Air Oil Systems, Mainland, Pa., or Berendsen Fluid Power, Rahway, N.J., or modified therefrom. The vibrator 203 is used to keep the grains free-flowing, with the intensity of vibration is set at a level that does not cause substantial aggregation of the grains.

In place of a Venturi, a simple gas source can be provided to propel grains through the tube. In one embodiment, the gas source directs gas pressure towards the outlet of the mechanical device that feeds grains, the gas jet can be directed and adjusted to act to deagglomerate grains at that outlet.

Figure 12A:
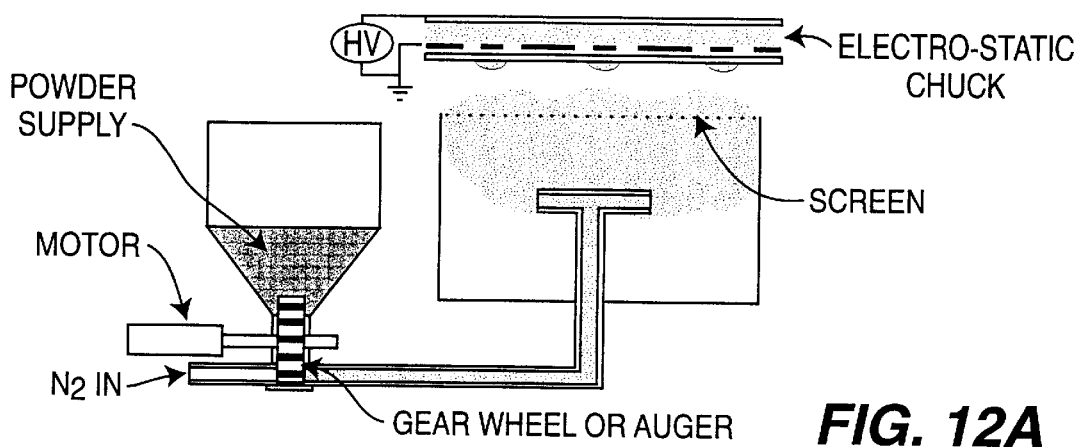
FIGS. 12A–12B show certain grain feed apparatuses that are alternatives to that illustrated in FIG. 10.
Figure 12B:
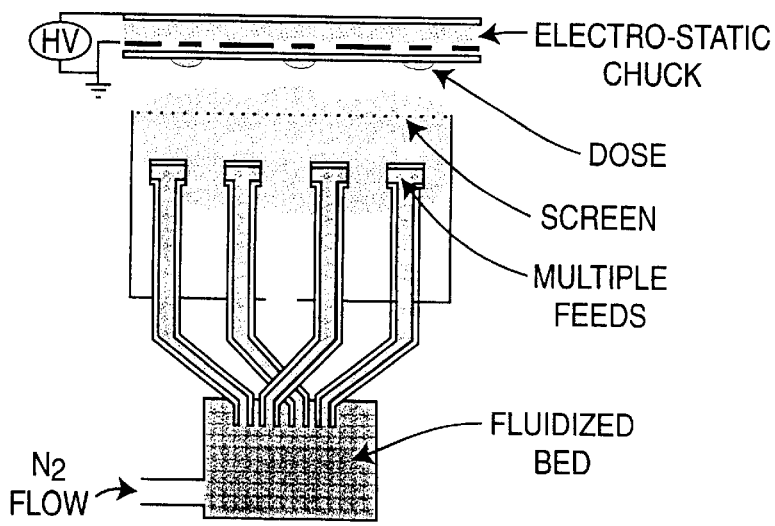

Other grain feed apparatuses can be used in the invention, such as the gear wheel apparatus illustrated in FIG. 12A. Hopper 222 directs grains to gear wheel 224 powered by motor 221. In FIG. 12B, fluidized bed 232 and gas flow directs grains through multiple powder feed tubes 237 (though of course one powder feed tube can be used). In some embodiments, particularly where doses such about 2 $\mu$g to about 50 $\mu$g or about 2 $\mu$g to about 100 $\mu$g are applied to an area of 3 to 4 mm diameter, a jet mill can be favorably employed to deliver grains. Charge can be introduced by induction charging by applying a potential to the jet mill itself, such as applying a 1,800V potential to the jet mill. A suitable jet mill is, for example, the TROST Air impact Pulverizer jet mill marketed by Plastomer Products Division of Coltec Industrial Products Inc. (Newton, Pa.). This jet mill utilizes directly opposing streams of compressed gas. The jet mill is usefully operated at a flow rate of about 2.0 to 2.2 liters per minute.

In one embodiment, the powder charging feed tube 207 is made of a material that imparts, by triboelectric charging, the appropriate charge to the powder as it transits tube making periodic collisions with the sides of the tube. For example, TEFLON® perfluorinated polymer) is often used to impart a positive charge to the grains (where appropriate for the grain material) and Nylon (amide-based polymer) is often used to impart a negative charge. In so charging the powder, the tube builds up charge which can, if not accommodated, discharge by arcing. Accordingly, a conductive wrap or coating is applied to the exterior of the tube and grounded. For example, the tube can be wrapped with a foil such as an aluminum or copper foil, or coated with colloidal graphite product such as AQUADAG® (Acheson Colloids Co., Port Huron, Mich.). Alternatively, the tube can be coated with a composition made up of graphite or another conductive particle such as copper or aluminum, an adhesive polymer, and a carrier solvent, with care taken to mix the components in amounts that preserve the tackyness of the adhesive component. An example of such a composition is 246 g trichloroethylene, 30 g polyisobutylene and 22.5 g of graphite powder.

The charge relieved by the grounding procedures outlined above can be monitored to provide a measure of grain flux through the powder charging feed tube 207. This data can be sent to the central electronic processor 410, which can use it to modify various parameters of the dry powder deposition apparatus. For example, a capacitor can be put in series with the powder charging feed tube 207 and serve to lower the potential generated by the charges collected in the powder charging feed tube 207. A 1 $\mu$F capacitor will build up 1V for a 1 $\mu$C charge. The other pole of the capacitor is connected to ground. The capacitor acts to bring the potential of the powder charging feed tube 207 closer to ground. An electrometer connected to the capacitor provides an accurate measure of collected charge. With a powder charged to 50 $\mu$C/g, 1 $\mu$C corresponds to 20 mg of powder. The powder charging feed tube 207 can be biased. With a bias applied to the tube of 500V, noise of 10 pA can be anticipated, creating an uncertainty of 3 nC over 3 minute intervals. Even with such biasing the system can give errors as low as 0.3% on measurement of 20 mg of powder. By controlling the conductivity of the grounding wrap or coating, a potential drop along the tube can be established, creating an electronic field which favors drawing charged powders through the tube while giving uncharged powders greater opportunity to pick up charge.

Another way to impart charge to the grains is by induction charging. For instance, a portion of the powder charging tube 207 can be an induction-charging tube such as a stainless steel tube biased by one pole from a power supply, with the opposite pole grounded. With an appropriate bias, an electric field is created in the induction-charging tube such that grains passing through it pick up a charge. The length of the induction-charging tube can be adjusted to sufficient length to assure the amount of charging desired. In one embodiment, induction charging is used in conjunction with the tribocharging features described above.

Figure 13:
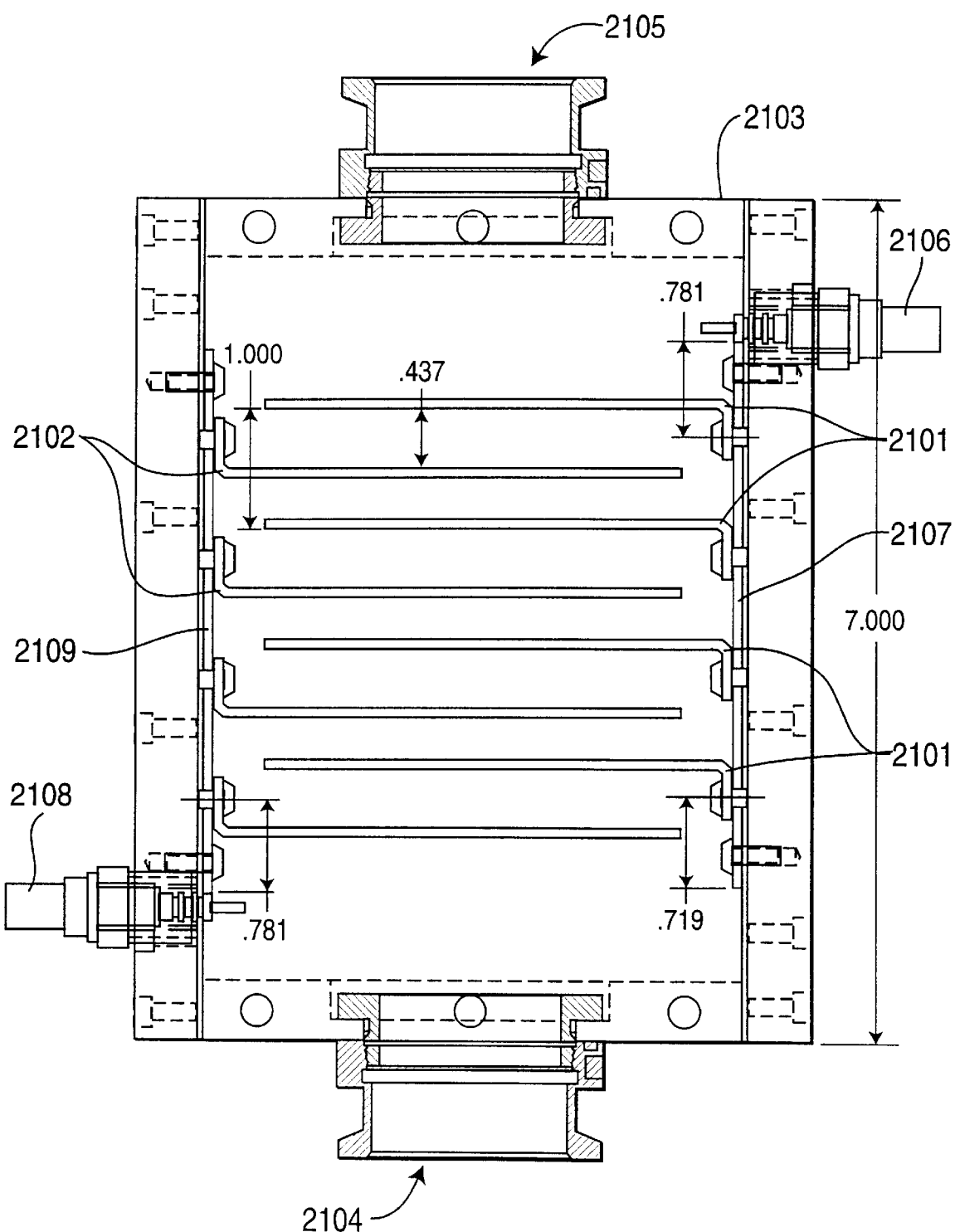
FIG. 13 illustrates a powder trap used for recovering materials that are not deposited on the substrate.

Grains (powders) that are not utilized at the deposition station are drawn back by a pressure differential through powder evacuation tubes 208 to powder trap 210 via trap inlet 2104. Illustrated in FIG. 13, powder trap 210 has a series of conductive first baffles 2101, such as copper, stainless steel or aluminum baffles, interleaved with conductive second baffles 2102. The baffles are affixed to first trap electrical conduit 2107 and second trap electrical conduit 2109, respectively, which are in turn affixed to trap body 2103, which is for example formed of acrylic polymer (Plexiglass). The first baffles are biased at, for example, +2,000V, via first trap electrical conduit 2107, which is biased via first electrical inlet 2106. The second baffles are biased, for example, at −2,000V, via second trap electrical conduit 2109, which is biased via second electrical inlet 2108. Grains returning from the deposition station are collected on oppositely charge baffles. Where grains are uncharged, a first collision with one baffle can impart a charge, allowing the grain to be attracted to a later baffle. Gas exiting the powder trap 210 via powder trap outlet 2105 is conveyed to a HEPA filter (not shown), providing an industrial safety feature assuring that significant amounts of powder, which can be detrimental as bioactive agents (without dosing control), are not released into the environment.

Shutdown of the deposition process, for example as a result of feedback data such as from the charge sensor or pursuant to a timing schedule (where the amount of a deposition is determined by the time of operating the deposition process), involves reducing the voltage (or the amplitude in the case of a pulsed voltage profile) directed to the grain-attracting electrodes, and shutting down the grain feed apparatus. The amount of voltage reduction appropriate will vary depending on such factors as the substrate, the grains and the level of grains applied, but is generally selected to maintain substrate and grain adherence to the substrate without substantially attracting further grain accumulation. For example, the deposition voltage (or the voltage amplitude where an pulsatile voltage is utilized) can be 2,000V, and this is stepped down to 400V to retain grains but not attract further grains.

Figure 19A:
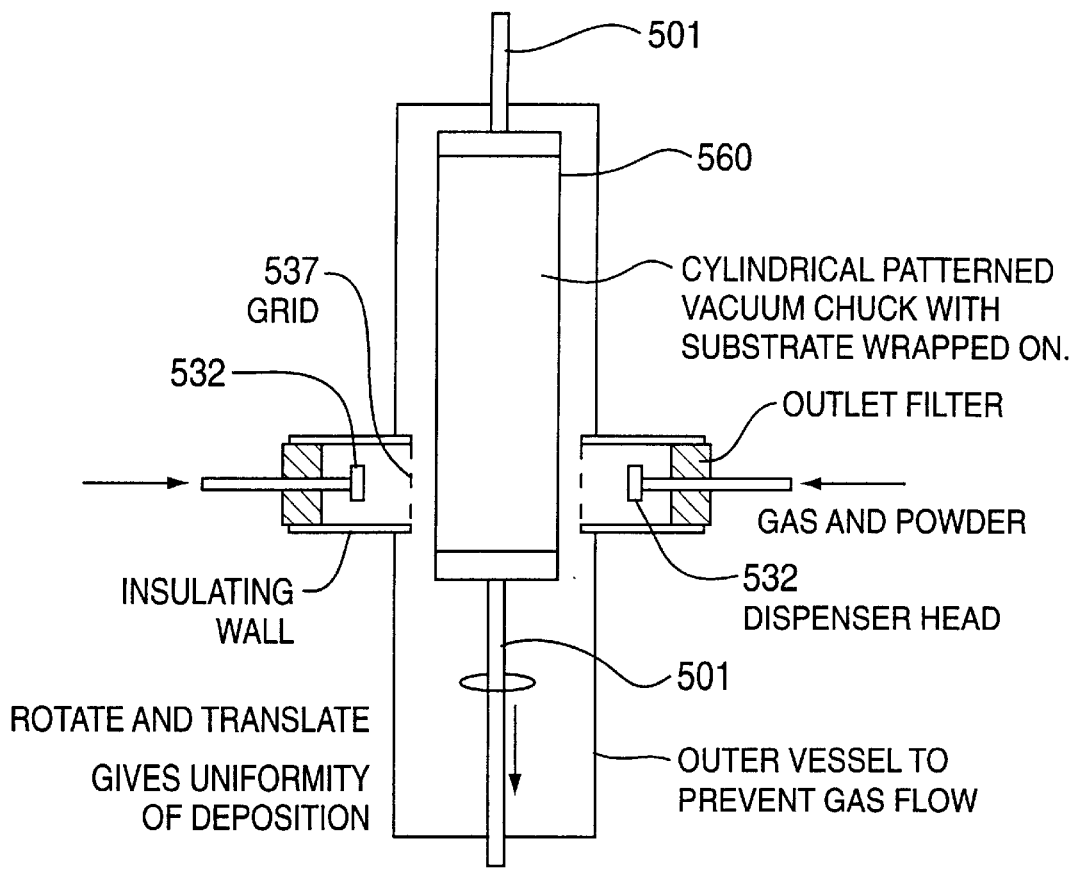
FIG. 19 shows a deposition system with attached electrostatic chuck that is a rotating drum.
Figure 19B:
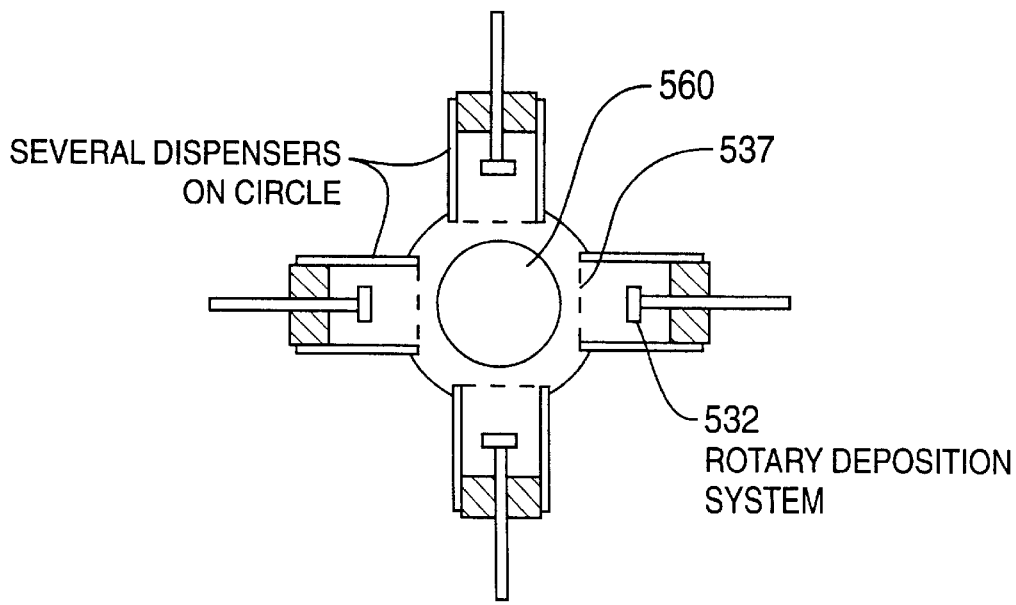

In one embodiment, exemplified in FIG. 19 the nozzles 532 are positioned around a receiver 560 with attached electrostatic chuck that is a rotating drum. Axles 501 can impart rotation to the receiver 560 and convey (e.g., through internal conduits) vacuum or electrical potential to the electrostatic chuck. The axles 501 can also be used to move the receiver up and down relative to the nozzles 532. Grids 537 limit access by improperly charged grains to the collection zones. FIG. 19A shows a side view, while FIG. 19B shows a top view. By rotating the receiver 560, variations in the deposition pattern can be minimized.

Several of the components recited herein can contribute to decreasing compaction of grains, to more uniform grain flux, ease of grain loading, operating stability, the ability to use a wide variety of grain particle sizes, and to avoid making surface modifications to the grains which in other contexts are used to keep powders free-flowing. The present invention is intended to be applicable in contexts, such as pharmaceuticals, where modifications to the grains can raise regulatory issues.

Dose Measurement Station

First robotic head 110 (e.g., see FIG. 2) moves the frame 50 containing a substrate 40 to dose measurement station 140. Note that to align the frame 50 with measurement opening 172, the robotic head is again rotated 90°. Receiver locating pins 1650 are used to closely establish the alignment of the receiver 160 with the measurement opening 172. This alignment helps assure that the measurements are made at the same locations as the depositions, for example to a accuracy of about ±0.5 mil. Of course, other alignment methods can be used, such as having the detection equipment at the dose measurement station 140 run preliminary scans to establish to locations of the collection zones CZ.

The illustrated dose measurement station 140 uses two optical measurement methods: diffuse reflection and optical profilometry. Diffuse reflection has been used for many years to characterize powders, using light sources that emit in a range that is absorbed by the powders. In the development of this technology, a theory was developed for diffuse reflection using non-absorbing radiation, which derived a term for the thickness of a powder layer. It is believed that no commercial development has been made from this latter theory. Applicants have now found that this measurement gives a strong correlation with deposited amount, at least up to certain amounts, which amounts vary with the character of the powder and are believed to correspond to amounts past which light penetration into lower layers is prevented.

Diffuse reflection is based on the reflection or scattering of a laser beam or a probe light beam off of the powder surface into directions that are not parallel to the specular (mirror-like) reflection direction. This scattered light is generally uniformly distributed in all directions. Dose depositions which exhibit this property are said to be "Lambert Radiators", where Lambertian scattering is an important property for dose weight measurements. The relation between the Lambertian scattering and the optical properties of powders is defined by the scattering model of Kubelka and Munk.

As described above, non-absorbing radiation is used to create diffuse reflection. Typical radiation is the visible red lines provided by common gas and diode lasers such as 632.8, 635 and 670 nm. When non-absorbing radiation is used and when the dose deposition is of a finite thickness, d, the Kubelka-Munk model gives the following relation:

$$Sd = R/(1-R) \quad (1)$$

where S is a scattering parameter defined by the properties of the particles of the dose powder, d is the powder dose thickness and R is the measured diffuse reflection for dose material on substrates with minimal specular diffuse reflectance wherein $R_{substrate}=0$ is assumed.

This equation can be expressed in the following formula, $$d = (1/S)\,[R/(1-R)] \quad (2)$$

wherein S is assumed to be a constant for a given particle size distribution. Thus, the thickness of the powder dose is directly related to the measured diffuse reflectance. If the dose is a Lambertian radiator, as previously defined, the measurement of R is available.

Figure 15A:
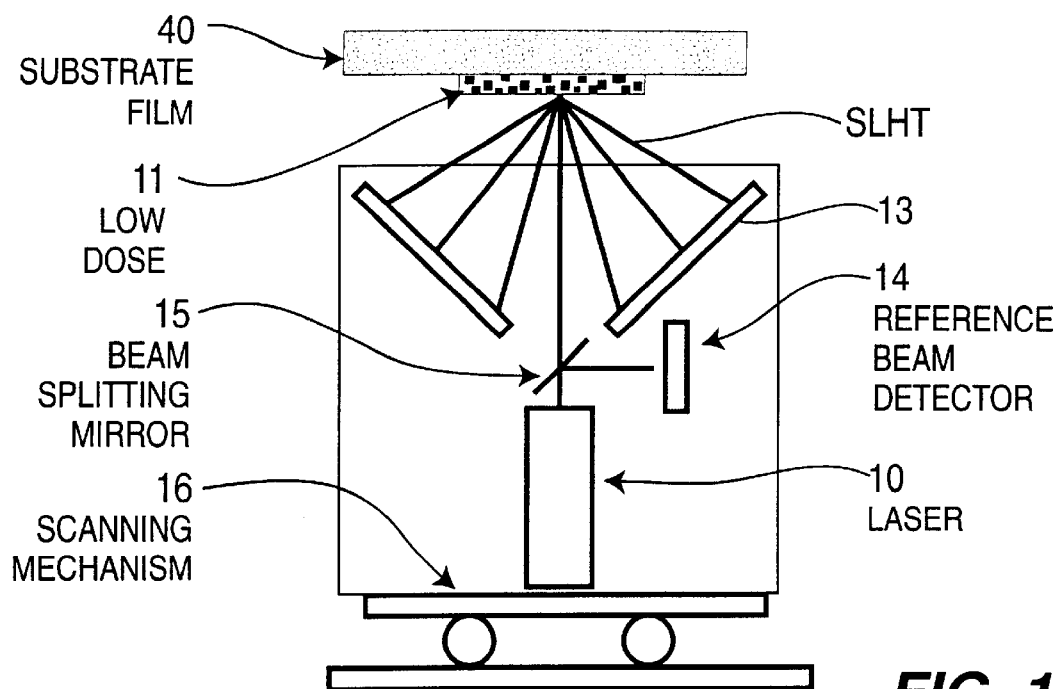

Shown in FIG. 15A is a schematic illustration of diffuse reflection for characterizing dry powders. When a light source 10 (such as a low energy laser) impinges on the deposited powdered particles 11, the particles scatter light SLHT in all directions. The light source is preferably focused through a beam splitting mirror 15. A reference beam detector 14 assists in determining the quality and intensity of the focused beam. The scattered light SLHT is captured by an array of preferably two or more detector zones 13. For example, there can be 1, 2, 3, 4, 5, 6, etc. detector zones. It may be advantageous to use amplifiers (not shown) with the detectors. The output from the detector zones is then connected to a commercial A/D converter (not shown). The resulting digital signal is scanned by using a computer controlled scanning mechanism 16, which is in communication with central electronic processor 410, to generate powder thickness profile and thus the dose weight measurements of the depositions. The light source can direct a beam that is wider than the relevant collection zones, since regions outside the collection zones will not have powder that gives rise to Lambertian scattering.

In one preferred embodiment, the powder can be deposited on a substrate that has a surface that is specular (having the qualities of a mirror) so that the contribution of the planar substrate 40 surface to the diffuse reflected component is minimized. It is also preferred that the substrate 40 to be absorptive so that the measurement will not be sensitive to diffuse reflections off of its back surface or off of the surface of the receiver 160.

Diffuse reflection in non-absorbing region provides good accuracy in measuring dose deposition amounts ranging from 50–400 µg, or even as high as 750 µg to 1 mg, for a 3 or 7 mm deposition dot (such as a 4 mm deposition dot), depending on the characteristics of the powder. The diffuse reflection method can detect substantially less than a monolayer of powder. If the deposit is more than a monolayer, accurate measurement requires that the probe light beam partially penetrate the upper layers so that it can be affected by the reflection off of the lower layers. However, to exhibit Lambertian characteristics, there tends to be a practical limit to suitable thickness, depending on the powder. The diffuse reflection is also a measure of the physical uniformity of the dose deposits at the above ranges.

Figure 15B:
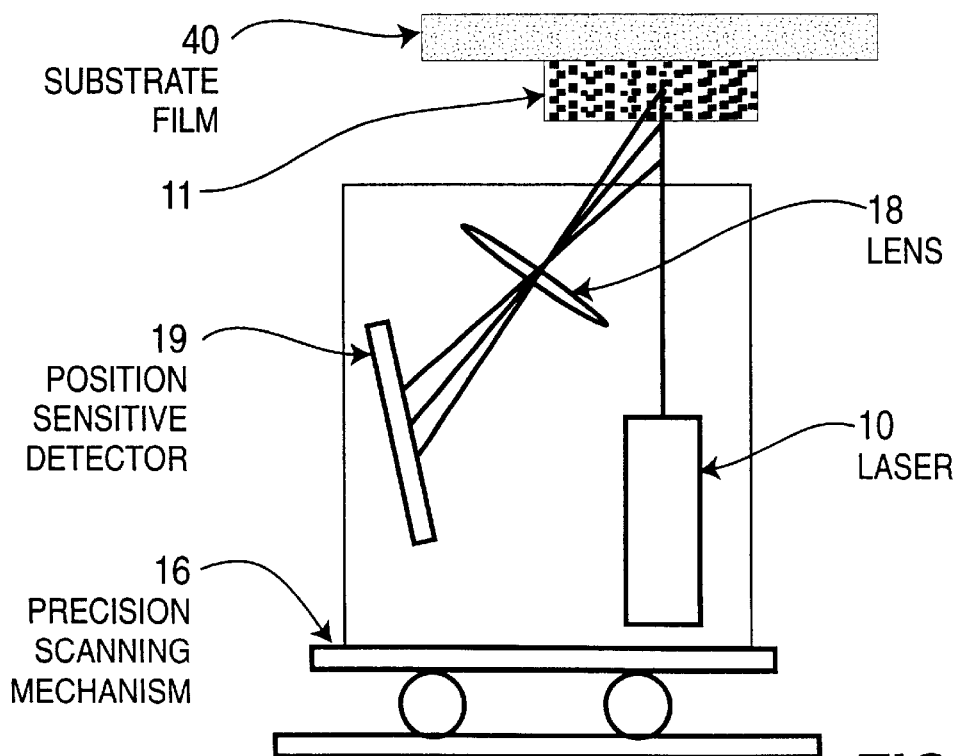
FIG. 15B shows a schematic representation of the optical profilometry method.

Optical profilometry is useful for the implementation of high dose measurements beyond the ranges that can be measured by diffusion reflection method. Shown in FIG. 15B is the schematic representation of the optical profilometry method. When a laser beam is focused on the deposition 11 light is deflected, with the angle of deflection indicative of the height of the deposition layer, which can be calculated by triangulation. The coherence of deflected light, which may be somewhat scattered, can be assisted by a profilometer lens 18 before the scattered light is captured by one or more position sensitive detectors 19. The output data from the detector is scanned by using a scanning mechanism 16 to generate profile of the powder surface.

The profilometer can be, for example, a confocal profilometer, meaning light is directed to the substrate through a lens system, and returned light passes at least in part through the same focusing system, though typically the returned light is reflected to a detection site. In one suitable confocal profilometer, a Model LT8105 from Keyence (Keyence Corp., Japan, or Keyence Corporation of America, Woodcliff Lake, N.J.), focuses source light through a pinhole, and a similar focusing through a pinhole of the return light helps establish focus. A source of back and forth movement applied to one of the lenses helps establish oscillations in the focus which help identify the optimal focus point. In one embodiment of the invention, a slit is used in place of a pin hole, and a spatially resolvable light detector, such as a charge-coupled device (CCD), is used to simultaneously retrieve data for multiple points along a linear area of the substrate. In some embodiments, there can be an issue of the grain-attracting electrode or some other feature of the receiver creating strong reflections that could overwhelm efforts to establish the baseline surface of the substrate. However, since the substrate is preferably uniform, these issues can be normalized away. Once material is deposited on the substrate, or where the substrate is sufficient opaque, clean reflections can be obtained.

The substrate can be scanned prior to deposition to increase the accuracy of the post-deposition scans. The beam is scanned across the surface and the height of the surface is established by triangulation. The difference between the profile after deposition and the pre-dose profile is attributable to the dose weight.

Since dry powders are generally good diffuse reflectors, it is also possible to use an optical triangulation system that is optimized for diffuse reflection. To determine the pre-dose surface profile, and to establish the height of the chuck during the post-dose measurement, it is preferred that the substrate surface 40 then so a diffuse reflector.

Figure 16:
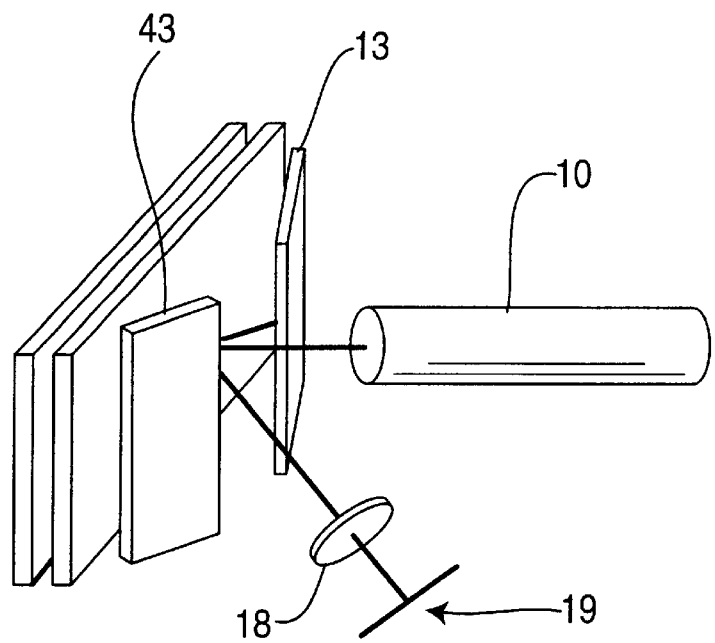
FIG. 16 show a substrate suitable for both profilometry and diffuse reflectance.

The surface, in any case, should preferably be absorptive so that the profilometer will not be confused by reflections off of the back surface of the substrate or off of the receiving system. Shown in FIG. 16 is one useful substrate suitable for both the triangulation profilometer and diffuse reflection systems. Striated substrate 43 has surface striations running in only one direction. The surface profile measurements are made by positioning the triangulation system with incident and reflected beams in a plane perpendicular to the striation direction. The striations thus act like a diffuse surface for this measurement. The diffuse reflection measurements are made in a plane that contains the striations. Ideally, striations do not scatter light in a direction parallel to themselves, so that any scattered light is attributable to the powder on the surface. For both measurements, the substrate can also be dyed so that reflections from the substrate's back surface or from the receiving system's surface not interfere with the measurement of either the profile or of the diffuse reflection.

For the sake of illustration only, a light source 10 is shown in FIGS. 15A–15B. However, more than one light source can be used to impinge on the powdered particles in different areas of a deposition site. The scattered light is captured by different detection zones.

In some embodiments, the deposition sites are excited in succession and powder profile is characterized after each light source excitation through the scanning mechanism 16 by moving the scanner, for example, from a first site to a second site and so on until all of the deposition sites are characterized. In some other embodiments, more than one deposition site is laser excited at a time and data is obtained by scanning the sites simultaneously. In such situations, it is desirable to optimize conditions for reducing the interference from nearby sites that are being characterized simultaneously. This can be accomplished by, for example, optimizing the spacing between the deposition sites or by alternating the excitations of different sites.

It is desirable that the laser be movable in different directions. An industrial process grade (x,y) stage 141 (see, FIG. 2) can assist the laser to move in the x,y direction. A solid state laser suitable for industrial applications such as, for example, LAS-200-635-5 from LaserMax Inc., (Rochester, N.Y.), can be used as a laser beam source, and mounted on detection platform 142 (FIG. 2) The detectors can be any suitable detector, preferably silicon, such as those sold by UDT Sensors, Inc., (Hawthorne, Calif.). Alternatively, large area solar cells can also be used.

It is often desirable to combine both of the dose measurement systems into a single system so that both the low dose and high dose measurements can be made and the range of the dose measurement is not limited by any single method used. In contrast to a system that combines the two modes of measurement with the use of just one light source, FIG. 18, discussed below, shows a system where measurement modes each have a separate light source.

In embodiments that do not use frames or another mechanism that helps assure that alignments at the deposition station and the dose-measurement station are the same, the dose-measurement system can be designed to identify the positions of the depositions. Such a mechanism could be a video camera that collects data, for example, in a charge-coupled device (CCD) and electronics to analyze the contents of the CCD to determine the boundaries of the depositions.

Figure 17:
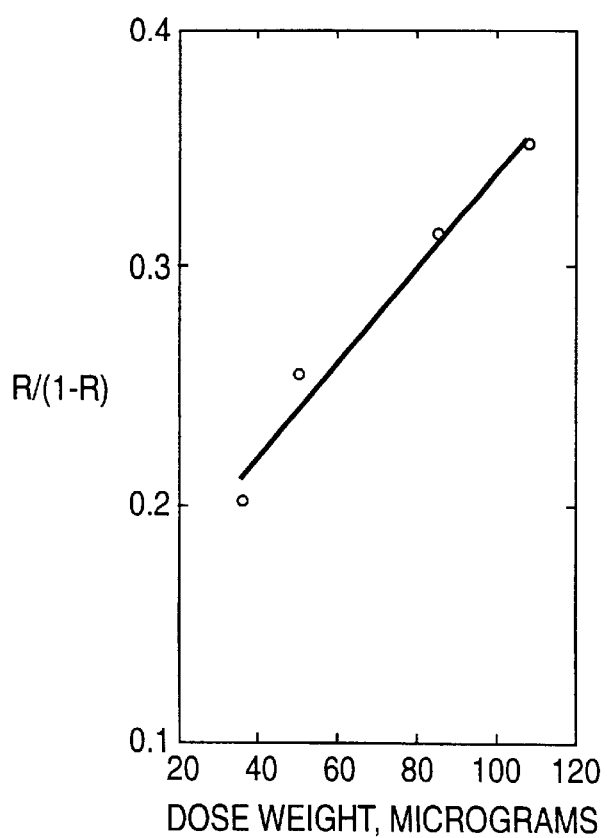
FIG. 17 shows diffuse reflectance data.

Polyethylene glycol (PEG) powder in an about 3 mm diameter dot has been deposited onto a MYLAR® substrate. The diffuse reflectance data were obtained using a laser (670 nm) based Keyence instrument (Keyence Corporation of America) operating in the "intensity" mode. Data was obtained using different, usually larger, fractions of the diffusely scattered light. The analytical properties of the measurement did not appear to be very sensitive to the fraction of collected light, i.e., the measurement is, in this context, unusually robust and ideal for use as an industrial measurement process. The data set forth in Table 1 below which was obtained using diffuse reflection method was the basis for the graph in FIG. 17, for the four points of this data set. The first three points were highly correlated and the least squares fit gave an R value, a measure of correlation, of 0.999. The fourth point showed variation and the least squares fit for the data set as a whole gave an R value of 0.98. Both R values were well within accepted norms for analytical procedures to determine dry powder dose weights.

TABLE 1

Experimental diffuse reflectance and dose weight data

| PEG Dose Weight, Micrograms, by Assay | Calculated R/(1-R) |
|---|---|
| 108.6 | 0.35 |
| 86.6 | 0.312 |
| 50.6 | 0.254 |
| 36.6 | 0.201 |

Subsequent measurements had shown that a high degree of correlation existed for the diffuse reflection and dose weight for various types of dose samples. Based on these data, the degree of correlation is thought to be related to the structure of the dose, specifically whether the structure exhibits Lambertian characteristics.

Figure 18:
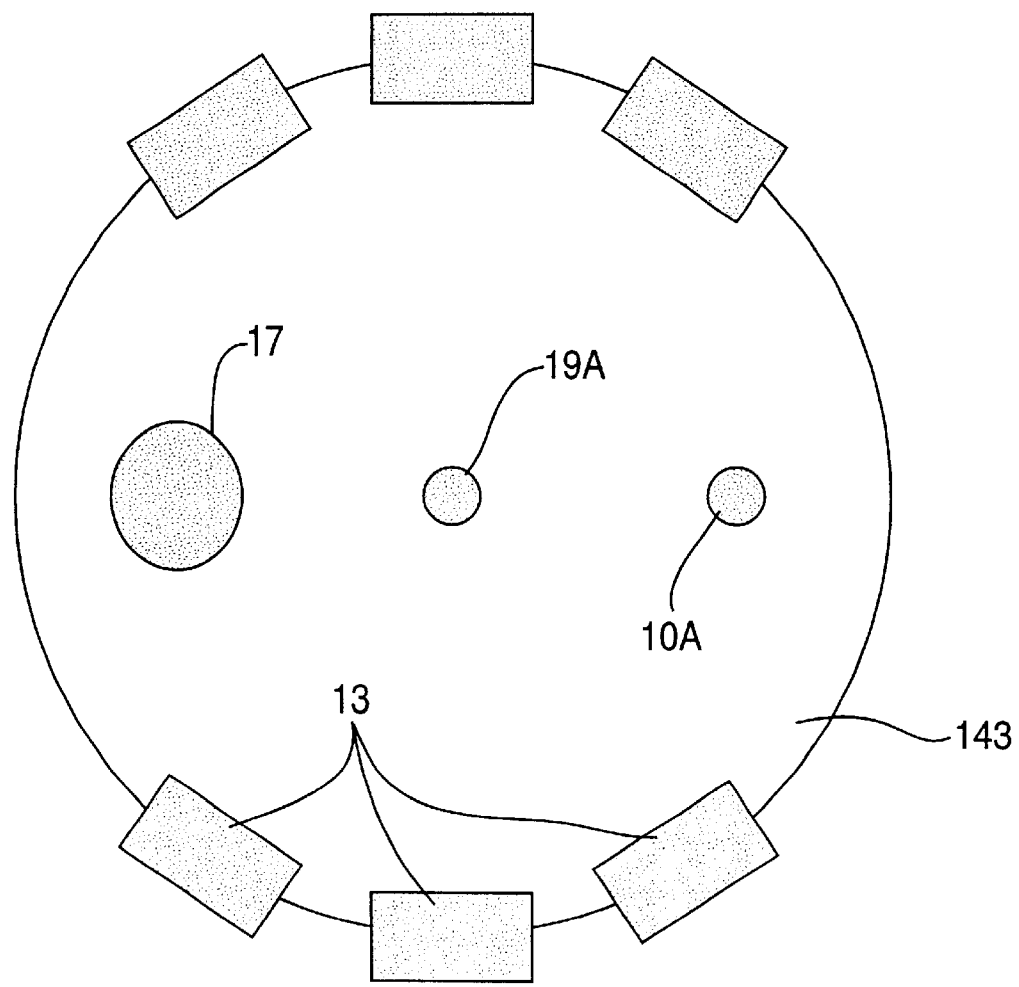
FIG. 18 shows a system where measurement modes each have a separate light source.

FIG. 18 illustrates a detection array on a detector support 143, which support can be positioned on detection platform 142. The detection array has a diffuse reflectance system made up of diffuse reflectance light source 10A and detection zones 13. A profilometry system is made up of profilometry light source lens 19A, which is part of a confocal system so that returned light passes through the same lens. The diffuse reflectance light source 10A is, for example, offset from the center point (where lens 19A is found) so that specular reflections, as opposed to diffuse reflections will be centered in an area such as area 17, and away from detector zones 13 (which are detectors that are preferably angled and designed to accept only light from the appropriate direction).

Application of a Covering Material

After dose measurement, the first robotic head 110 moves the frame 50 to lamination station 180, where frame 50 is deposited on top of second frame 50B in which is framed an indented covering substrate 42. Alignment mechanisms on the frames and at lamination station 180 assure that the locations with deposited grains are matched with the indentations in covering substrate 42, as illustrated in FIG. 14. At lamination station 180 there is a lamination support block 181, a portion of which is illustrated in FIG. 14. Lamination support block 181 has dimples into which the indentations of covering substrate 42 fit, and provides a support which presses the covering sheet against the planar substrate 41. Lamination support block 181 also provides a support against which the lamination tool on second robotic head 120 can rest while performing its function. Second robotic head 120 has vacuum cups 121 and ultrasonic welding head 122, as indicated in FIG. 2. After the first robotic head 110 moves away, second robotic head 120 moves into place and manipulates ultrasonic welding head 122 to seal all the depositions between layers of substrate. A suitable ultrasonic welding head is, for example, a 900 M-Series ultrasonic welder from Branson Ultrasonics Corporation (Danbury, Conn.). It will be recognized that other sealing methods are available, such as thermal or adhesive lamination. The illustrated bonding method is useful when one desires to keep the deposited grains free of admixture with other components such as film polymers, though it will be recognized that this can be achieved in other ways. The illustrated lamination process provides ultrasonic welds that ring the area on which material is deposited, but it will be recognized that more uniform lamination processes are also applicable.

In one embodiment of the invention, placebos are produced by laminating a substrate on which nothing was dry deposited, or on which an inactive substance was dry deposited.

Miscellaneous Considerations

A number of features are described herein with particularity about ancillary features. For instance, because the Applicants get particularly favorable results using one method of aligning the substrate in the same way with the deposition station 130 and the dose measurement station 160, the above discussion frequently mentions the frames that are used to help achieve this alignment. However, those of ordinary skill will recognize many of the features described herein will be useful without others that are described, such as a deposition apparatus that does not use frames that is readily envisioned by one of ordinary skill having benefit of this disclosure.

In preferred embodiments, the electrostatic chuck will be cycled out of the process and reused sooner than illustrated in the embodiment most particularly described above. For example, in embodiments where the planar substrate is a film that is advanced on rollers, the electrostatic chuck used in deposition can be brought in contact with the film when the film advances to the deposition station, and removed immediately thereafter. If necessary, another chuck can be used to assure that the film is smooth and flat (in most embodiments) when presented to a dose-measurement station. Such an embodiment with a roller-fed film will typically not use frames, though frames are an option as discussed above.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE

Using the techniques and apparatuses described herein, uniform depositions of ±5%, and ±3% of a target amount are obtained. Such depositions can include, for example, depositions onto 4 mm diameter collection zones of amount ranging from 2 $\mu$g to 50 mg.

Glossary

The following terms shall have, for the purposes of this application, the respective meaning set forth below.

delivery to an animal: A delivery device for delivering defined amounts of reagents to an animal delivers such defined amounts to a tissue of the animal. For example, the device can deliver reagents orally, sublingually, rectally, nasally, vaginally, topically (including the use of a patch or other transdermal delivery device), by pulmonary route (for instance by use of an aerosol or powder cloud), or parenterally (including, for example, intramuscularly, subcutaneously, intraperitoneally, intraarterially, intravenously or intrathecally).

dielectric or non-conductive: Materials referred to as dielectric or non-conductive are non-conductive to a degree that distinguishes them from such conductive materials as copper and the like. The degree of non-conductance can vary considerably with the context.

dry deposited: A material is "dry deposited" if deposited without applying the material in a liquid vehicle.

excipient: Excipients are pharmaceutically acceptable organic or inorganic carrier substances suitable for parenteral, enteral (e.g., oral or inhalation) or topical application that do not deleteriously react with the active compositions. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxymethylcellulose, polyvinylpyrrolidinone, and the like.

effective amount: The meaning of "effective amount" will be recognized by clinicians but includes amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease, or the symptoms thereof.

electro-attractive dry deposition: This term refers to methods that use an electromagnetic field, or an electrostatically charged surface to dry deposit charged grains (e.g., particles).

grains are, for the purposes of this application, either aggregates of molecules or particles, typically of at least about 3nm average diameter, preferably at least about 500 nm or 800 nm average diameter, and are preferably from about 100 nm to about 5 mm, for example, about 100 nm to about 500 $\mu$m. Grains are, for example, particles of a powder, or polymer structure that can be referred to as "beads." Beads can be coated, have adsorbed molecules, have entrapped molecules, or otherwise carry other substances.

planar substrate is intended to denote a substrate which is predominately formed with two major dimensions, such as a tape or sheet. The term does not imply that the substrate is flat.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method for depositing grains on a substrate comprising:

providing an electrostatic chuck having one or more collection zones;

placing a substrate on one or more of the collection zones;

directing charged grains towards the substrate;

collecting sensor input data at an electronic processor, including input data from one or more deposition sensors placed on or adjacent to the electrostatic chuck for measuring the amount of grains deposited at the one or more deposition sensors;

operating the electronic processor to respond to data from the one or more deposition sensors by adjusting, as indicated by the data, current deposition parameters comprising one or more of (a) flux of grains through an apparatus directing the grains and (b) voltages applied at one or more collection zones to attract grains;

electrostatically depositing the gains on the substrate at the locations of the collection zones;

detecting, after the depositing step, the amount of grains deposited at locations corresponding to the locations of the collection zones; and sending the deposition data to the electronic processor, which uses the deposition data to adjust deposition parameters for a subsequent iteration of the method.

2. The method of claim 1, further comprising collecting, at the electronic processor, sensor inputs measuring the flux of grains directed in the grain directing step.

3. The method of claim 1, wherein the detecting after the deposition step is done by diffuse reflectance.

4. The method of claim 1, wherein the detecting after the deposition step is done by optical profilometry.

5. A method for depositing grains on a substrate comprising:

providing an electrostatic chuck having one or more collection zones, which electrostatic chuck is mounted on, and electrically connected to, a movable receiver comprising a voltage board comprising voltage converters for amplifying to higher voltages a voltage supplied by an external power source, placing a substrate on one or more of the collection zones;

directing charged grains towards the substrate;

applying, via the voltage board, the higher voltages to the electrostatic chuck to create grain-attracting fields at the collection zones, such that the higher voltages are localized in the electrostatic chuck where the higher voltages are needed; and electrostatically depositing the grains on the substrate at the locations of one or more of the collection zones.

6. The method of claim 5, further comprising:

operating an electric processor for controlling depositions, sending operating signals from the electronic processor to the movable receiver, which receiver further comprises an addressing board that assigns (a) locations on the electrostatic chuck receiving a voltage or voltage adjustment and (b) amplitudes of the voltages or voltage adjustments; and sending the assigned location and amplitude information to appropriate channels of the voltage board.

7. The method of claim 5, wherein the higher voltages are from 250V to 3,000V.

8. A method for depositing grains on a substrate comprising:

providing an electrostatic chuck having two or more separate collection zones;

placing a substrate on one or more of the two or more collection zones;

directing charged grains towards the substrate by:
  delivering grains towards the electrostatic chuck through a tube;
  feeding grains towards the tube; and
  operating one or more of:
    a gas driven Venturi having a Venturi well to pull the inserted grains and propel them, with the gas, through the tube, or
    a gas source directing gas towards the inserted in to separate grains and providing gas flow for propelling grains through the tube; and selectively electrostatically depositing the grains on the substrate at the locations of one or more of the collection zones.

9. A method of claim 8, wherein the grains pass from the feeding process, through the Venturi well, and into the tube in substantially a straight line.

10. The method of claim 8, wherein the feeding process comprises vibration for enhancing the fluidity of the grains.

11. The method of claim 8, wherein the feeding process comprises operating an auger.

12. The method of claim 8, comprising conducting the feeding with a gear wheel.

13. The method of claim 8, comprising inductively charging the powder as it passes through at least a portion of the tube.

14. A method for depositing grains on a substrate comprising:

providing an electrostatic chuck having two or more separate collection zones;

placing a substrate on one or more of the two or more collection zones;

delivering grains through a tube towards the electrostatic chuck;

applying charge to the grains by tribocharging induced by contacts between the grains and the tube or by induction charging caused by a potential applied to the tube; and selectively electrostatically depositing the grains on the substrate at locations of one or more of the collection zones.

15. The method of claim 14, further comprising:

discharging charge accumulations in the tube via a grounded conductive layer on the tube.

16. The method of claim 15, further comprising:

monitoring the amount of charge discharged from the tube; and operating an electronic processor that utilizes data from the monitoring as an indicator of the amount of grains passing through the tube to adjust the grain deposition process.

17. The method of claim 14, comprising applying charge to the grains by by induction charging caused by a potential applied to the tube.

18. The method of any one of claims 1, 2, 5–11, or 14–16, wherein the deposited grains comprise medicament.

* * * * *